United States Patent [19]
McCullough et al.

[11] Patent Number: 6,097,015
[45] Date of Patent: Aug. 1, 2000

[54] MICROWAVE PRESSURE VESSEL AND METHOD OF STERILIZATION

[75] Inventors: John V. McCullough; Charles L. Ice, both of Fort Worth; Jeremy W. Leonard, Dallas; Stephen Sherard, Richardson, all of Tex.

[73] Assignee: Healthbridge, Inc., Vancouver, Canada

[21] Appl. No.: 09/172,028

[22] Filed: Oct. 14, 1998

Related U.S. Application Data

[63] Continuation-in-part of application No. 08/651,920, May 21, 1996, abandoned, which is a continuation-in-part of application No. 08/446,442, May 22, 1995, abandoned, and a continuation-in-part of application No. 08/510,287, Aug. 2, 1995, Pat. No. 5,728,310.

[51] Int. Cl.[7] ..................................................... G05B 11/00
[52] U.S. Cl. .......................... 219/686; 219/695; 219/748; 219/749
[58] Field of Search ..................................... 219/695, 696, 219/697, 701, 686, 679, 746, 748, 750, 756, 762, 704, 707; 422/21, 302, 307; 588/212, 227, 900

[56] References Cited

U.S. PATENT DOCUMENTS

| | | | |
|---|---|---|---|
| 3,210,511 | 10/1965 | Smith | 219/748 |
| 4,006,338 | 2/1977 | Dehn | 219/697 |
| 4,276,462 | 6/1981 | Risman | 219/748 |
| 4,335,290 | 6/1982 | Teich | 219/749 |
| 4,477,707 | 10/1984 | Kim | 219/697 |
| 5,008,506 | 4/1991 | Asmussen et al. | 219/696 |
| 5,124,125 | 6/1992 | Brent | 422/21 |
| 5,180,895 | 1/1993 | Briggs et al. | 219/697 |
| 5,213,758 | 5/1993 | Kawashima et al. | 422/21 |
| 5,246,674 | 9/1993 | Katschnig et al. | 422/302 |
| 5,407,641 | 4/1995 | Katschnig et al. | 422/107 |

*Primary Examiner*—Mark Paschall
*Assistant Examiner*—Quang Van
*Attorney, Agent, or Firm*—Reed Smith Hazel & Thomas LLP

[57] ABSTRACT

A novel method and apparatus for sterilizing, disinfecting or otherwise heating materials, objects, liquids and the like under pressure is disclosed. The invention utilizes the generation and transmission of single-mode, non-interfering coaxial microwaves from multiple sources into the material to be treated. As a result, a more efficient transfer of microwave energy into the material to be treated is obtained.

26 Claims, 17 Drawing Sheets

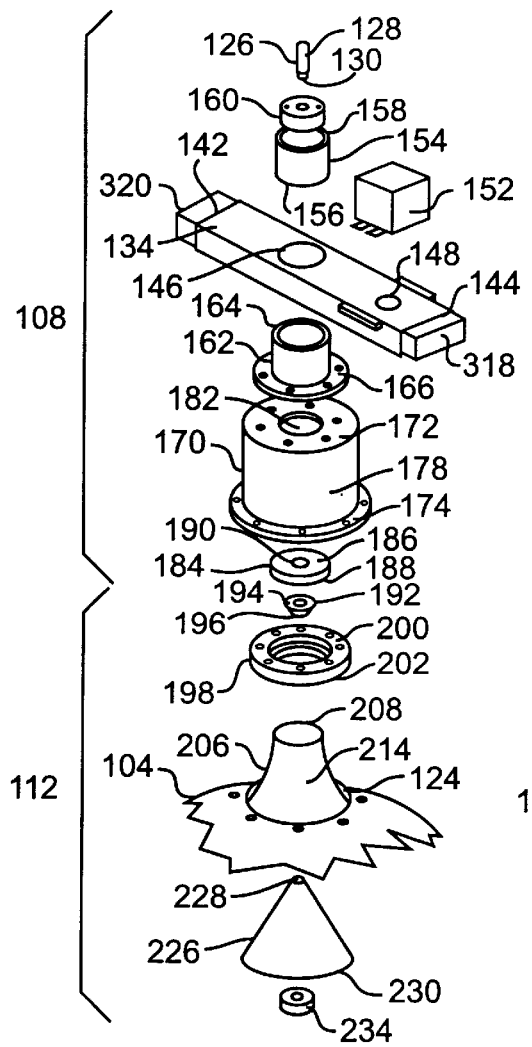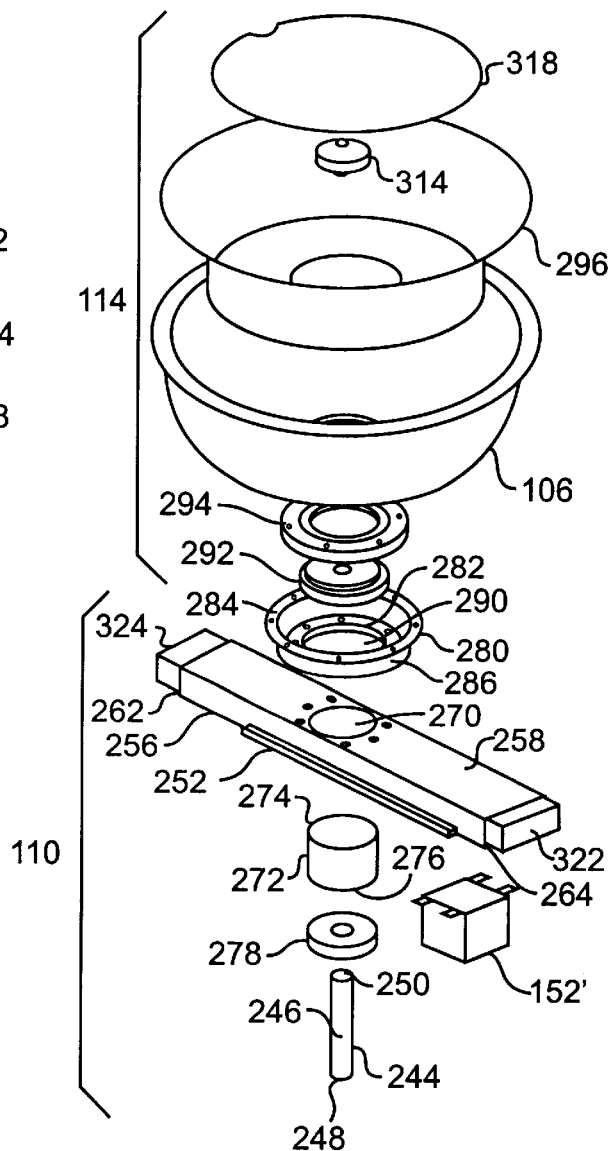
FIG. 9   FIG. 10

MICROWAVE PRESSURE VESSEL AND METHOD OF STERILIZATION

RELATED APPLICATIONS

This application is a continuation-in-part of U.S. application Ser. No. 08/651,920 abandoned, filed May 21, 1996, which is a continuation-in-part of U.S. application Ser. No. 08/446,442 abandoned, filed May 22, 1995, and a continuation-in-part of U.S. application Ser. No. 08/510,287 U.S. Pat. No. 5,728,310 filed Aug. 2, 1995.

TECHNICAL FIELD

The present invention relates to a novel method and apparatus for use of microwave energy to make a pressure heating vessel. In a preferred embodiment, the invention relates to a novel apparatus and method for sterilizing medical waste.

BACKGROUND OF THE INVENTION

The present invention relates to a microwave apparatus and method for heating materials, objects, liquids or the like under pressure. In one aspect, the invention can be used for the sterilization of medical wastes by means of microwave energy used to generate sufficient heat and pressure to sterilize. While the invention will be described in relation to the preferred embodiment tailored for medical wastes, it will be apparent that it is suitable for a wide range of applications.

Medical waste is infectious refuse that can transmit a wide variety of diseases. Generators of medical waste include hospitals, doctors' offices, clinics, dental offices, laboratories, research facilities, nursing homes, and funeral parlors. As medical costs rise, an ever-increasing number of long term illnesses are being treated at home, the result of which is medical waste mixed with ordinary household trash. Additionally, the quantity of medical waste has dramatically increased in recent years due to the expanded use of disposable, rather than reusable, products.

In many jurisdictions, the definition of medical waste has been broadened to include an ever-widening variety of materials. The Center for Disease Control has issued recommended procedures whereby any material that comes into contact with any patient's body fluids be treated as if it were infectious. Examples of such waste include bandages, gloves, tubing, syringes, laboratory cultures, and pathological wastes. Furthermore, in response to an increase in illegal medical waste disposal, most states have enacted statutes and regulations on the handling of medical waste from large- and small-scale generators. In addition, the federal Medical Waste Tracking Act created a lifetime tracking system for infectious waste. Before sterilized waste can be disposed of as noninfectious, it must be rendered unrecognizable compared to its original form.

Typically, waste which is generated is isolated in special sealed containers until it can be treated. Except for using chemical treatment, all infectious bacteria, viruses and organisms are normally destroyed by some form of heat. The most widely used forms of heat treatment are autoclaving, i.e., sterilization with steam, and burning at specially equipped incineration sites. Both retrofitting existing hospital incinerators and building new environmentally acceptable incinerators are extremely costly alternatives, while conventional autoclaving is often too slow and costly. Conversely, on-site treatment greatly reduces disposal costs because the material need not be treated as hazardous. A rapid, on-site, low cost treatment for sterilizing or otherwise treating medical waste is, therefore, very desirable.

Sterilization has a number of definitions including those promulgated by the regulating agencies of various jurisdictions and the various definitions adopted by medical research facilities. For purposes of this application, "sterilization" means conditions sufficient to obtain a log $10^6$ reduction of the spore forming bacteria, *bacillus stearothennophilus*. The description contained herein is of an apparatus and method which will achieve that standard. Obviously the apparatus and method can also achieve lower standards. For purposes of this application, "disinfection" means any treatment not meeting the requirements of sterilization.

The method of sterilization generally acknowledged to be most reliable is autoclaving, which entails the heating of items to at least about 212° F. in a steam saturated atmosphere for periods of time ranging from about ten minutes to one day or more. Pressurized steam sterilization of instruments by autoclaving has been done by hospitals and medical offices for many years. However, large-scale sterilization of medical waste is possible only if steam is able to penetrate voluminous waste for a sufficient time at a sufficient pressure and temperature to effect essentially complete sterilization of all the wastes no matter what their location within the larger container. To this end, a pressure vessel is required in order to achieve sterilization as opposed to a vessel which is open to normal atmospheric conditions. After autoclaving or incineration which is sufficient to sterilize waste, residues can be deposited in landfills.

Another method of sterilization commonly used is dry heat. However, dry heat sterilization requires a lengthy period of heating. Other sterilization methods successfully used in limited situations include chemical vapor sterilization, bacteriocidal chemical treatment, and liquid disinfectant usage.

Recently, an interest has arisen in using microwave energy for sterilization. See, e.g., U.S. Pat. Nos. 5,098,665; 5,124,125; 5,213,758; 5,246,674; and 5,223,231. The devices of these patents transmit multimode microwaves. Thus, they are relatively inefficient in transmitting microwave energy to the load to be treated. In addition, these devices can only propagate or transmit the microwaves in a linear fashion.

Thus, there remains a continuing need for a quick, reliable and inexpensive way to locally sterilize infectious waste, and for a device which will permit the use of microwave energy in a pressure vessel. The present invention answers these needs and has the following advantages:

(a) it allows a more efficient use of microwaves to sterilize in a pressure vessel;

(b) it increases the energy efficiency of microwave ovens;

(c) it provides, in the sterilization embodiment, a device which can produce sufficient heat to sterilize throughout the entire volume of waste;

(d) it provides, in the preferred sterilization embodiment, a compact apparatus that does not require drains;

(e) it provides an automatic control of processing; and (f) it provides an apparatus that is highly efficient in transmitting energy to the containment vessel.

OBJECTS OF THE INVENTION

One object of the invention is to provide a microwave waste sterilizer that is highly efficient in the use of the microwave energy which is broadcast.

Another object of the invention is to provide a microwave waste sterilizer that allows waste containers used in the sterilization process to be reused.

Another object of the invention is to provide a microwave sterilization process that can recycle the moisture added and condensate formed during the process.

Another object of the invention is to provide a microwave sterilization process that generates all necessary pressure internally, thus eliminating cold spots.

It is yet another object of the invention to provide a process of introducing microwave energy into a chamber in a uniform and dispersed pattern.

SUMMARY OF THE INVENTION

The present invention relates to a pressure vessel utilizing microwave energy. The vessel includes a first wall member defining a first portion of the pressure vessel and a second wall member defining a second portion of the pressure vessel. The first and second pressure hulls are releasably and sealably closable. At least one of the walls has a portion thereof constructed of a material substantially transparent to microwaves. The apparatus further comprises a coaxial microwave generating assembly operatively positioned adjacent to the portion of the pressure hull which is substantially transparent to microwave energy to provide for the transmission of coaxial microwaves into the pressure vessel.

In one embodiment of the invention, there is provided a microwave waste sterilizer comprising an upper outer shell, a lower outer shell, an upper means for guiding microwave energy connected to the upper outer shell, a lower means for guiding microwave energy connected to the lower outer shell, an upper means for dispersing microwave energy connected to the upper means for guiding microwave energy, a lower means for dispersing microwave energy connected to the lower means for guiding microwave energy, and a releasable clamp assembly holding the upper outer shell and the lower outer shell together.

In another aspect, the present invention relates to a pressure vessel which is releasably and sealably closable and which has at least one portion made from a material substantially transparent to microwaves which defines a passageway therethrough. Adjacent to the microwave transparent portion of the pressure vessel is a coaxial microwave generating assembly having a magnetron, waveguide and linear element extending from the output end of the waveguide. The coaxial microwave generating assembly is operatively positioned adjacent to the portion of the pressure hull which is transparent to microwave energy such that the linear member passes through the passageway of the substantially transparent material. In the preferred embodiment, the linear member defines a passageway through which fluids such as water may be injected into the pressure vessel. In a preferred embodiment, a conical member is attached to the to outside of the linear element such that the base of the cone is adjacent to the end of the linear element extending into the pressure vessel. Further, in this preferred embodiment, the pressure vessel hull, or a liner provided therein, is shaped in a parabolic form. The cone and parabola are tuned such that a coaxial microwave field is established in the majority of the pressure vessel.

The invention also relates to providing a pressure vessel as described above in which a nozzle is attached to the end of the linear element extending into the pressure vessel to permit emission of a spray of water into the vessel. Preferably the spray pattern is tuned such that small droplets of water are thrown into the path of the microwaves entering the unit, are heated and are flashed to steam. It is preferred that the specific spray pattern be selected such that it optimizes the heating of the injected water by the microwaves.

In another aspect, the present invention relates to an apparatus suitable for the sterilization of waste material. The apparatus comprises a pressure vessel which is releasably and sealably closeable. The pressure vessel has an upper portion having at least one section made of a material substantially transparent to microwave energy, said material defining a passageway therethrough. The lower portion of the pressure hull has a second section of material substantially transparent to microwave energy, said material defining a passageway therethrough. Within the lower portion of the pressure vessel is a floor made of material substantially transparent to microwave energy. Positioned in operative association with the substantially transparent microwave portions of the pressure hull are coaxial microwave generating assemblies. These coaxial microwave generating assemblies include a linear element around which the microwaves can couple and thereby form a coaxial microwave. The linear elements extending from the coaxial microwave generating assemblies pass through the passageways of the substantially microwave transparent material that form portions of the pressure hull. In the preferred embodiment, at least one of the linear elements defines a passageway through which water may be injected into the pressure vessel. In a preferred embodiment, at least one of the linear elements defines a passageway allowing the drainage of condensate and steam therethrough. At the second end of the drainage or outlet passageway is a flash chamber to flash steam to a condensate. The flash chamber has two exit conduits, one to a filter which exhausts to the atmosphere, and the other a drain conduit for liquid which is connected to a liquid storage reservoir.

In another aspect, the present invention relates to a coaxial microwave generating assembly comprising a waveguide having a first and second end, and a magnetron adjacent to the first end for generating microwave energy. The waveguide defines an axis and at the second end of said waveguide is a linear element adjacent to the second end which is coaxial with the axis of a waveguide. In the preferred embodiment, the invention relates to a coaxial microwave generating assembly having a "t" shaped waveguide with a main waveguide section having a first and second end. Proximate to the first end thereof is a magnetron for generating microwaves. At the second end of the main waveguide section are a first reflective waveguide section and an output waveguide section each defining an axis. The axes of the first reflective waveguide section and the output waveguide section are perpendicular to the axis of the main waveguide section. The axes of the first reflective waveguide section and the output waveguide section are preferably coaxial. Adjacent to the first reflective waveguide section and output waveguide section is a second reflective waveguide section defining an axis. Preferably the axis of the second waveguide section is coaxial with the axis of the main waveguide section.

Passing through the waveguide's output portion is a linear member having an axis, and said axis being coaxial with the axis of the output waveguide. In the preferred embodiment, this linear member is a conduit defining a passageway through which liquids such as water may be injected through the coaxial microwave generating assembly.

In another embodiment of the invention, there is provided a method for sterilizing waste materials. The method comprises placing waste materials in a reusable plastic waste or fiberglass container, placing the waste container in a microwave waste sterilizer, broadcasting an upper magnetron and a lower magnetron simultaneously so as to generate microwaves within the microwave waste sterilizer to heat the microwave waste sterilizer in the presence of water to a predetermined pressure, maintaining the pressure for a predetermined time period, stopping the generation of microwaves, releasing the pressure until near atmospheric conditions exist within the microwave waste sterilizer, opening the waste sterilizer, and removing the waste container.

In yet another embodiment of the invention, there is provided a method for dispersing microwave energy into a chamber. The method comprises broadcasting microwave energy across a chamber, reflecting the microwave energy from a surface of the chamber, coupling the microwave energy onto a means for coaxial guidance, changing a first direction of flow of the microwave energy to a second direction of flow substantially parallel to the means for coaxial guidance, propagating the microwave energy in the second direction of flow within a means for guiding microwave energy, separating the microwave energy in a means for dispersing microwave energy, and creating a flux field of substantially uniform flux.

BRIEF DESCRIPTION OF THE DRAWINGS

The invention may be more readily understood from the following drawings together with the detailed description. The drawings are not restrictive of the invention, but rather, illustrative.

FIG. 9 is an exploded view of the upper sections.

FIG. 10 is an exploded view of the lower sections.

DETAILED DESCRIPTION OF THE PREFERRED EMBODIMENTS

Figure 1:
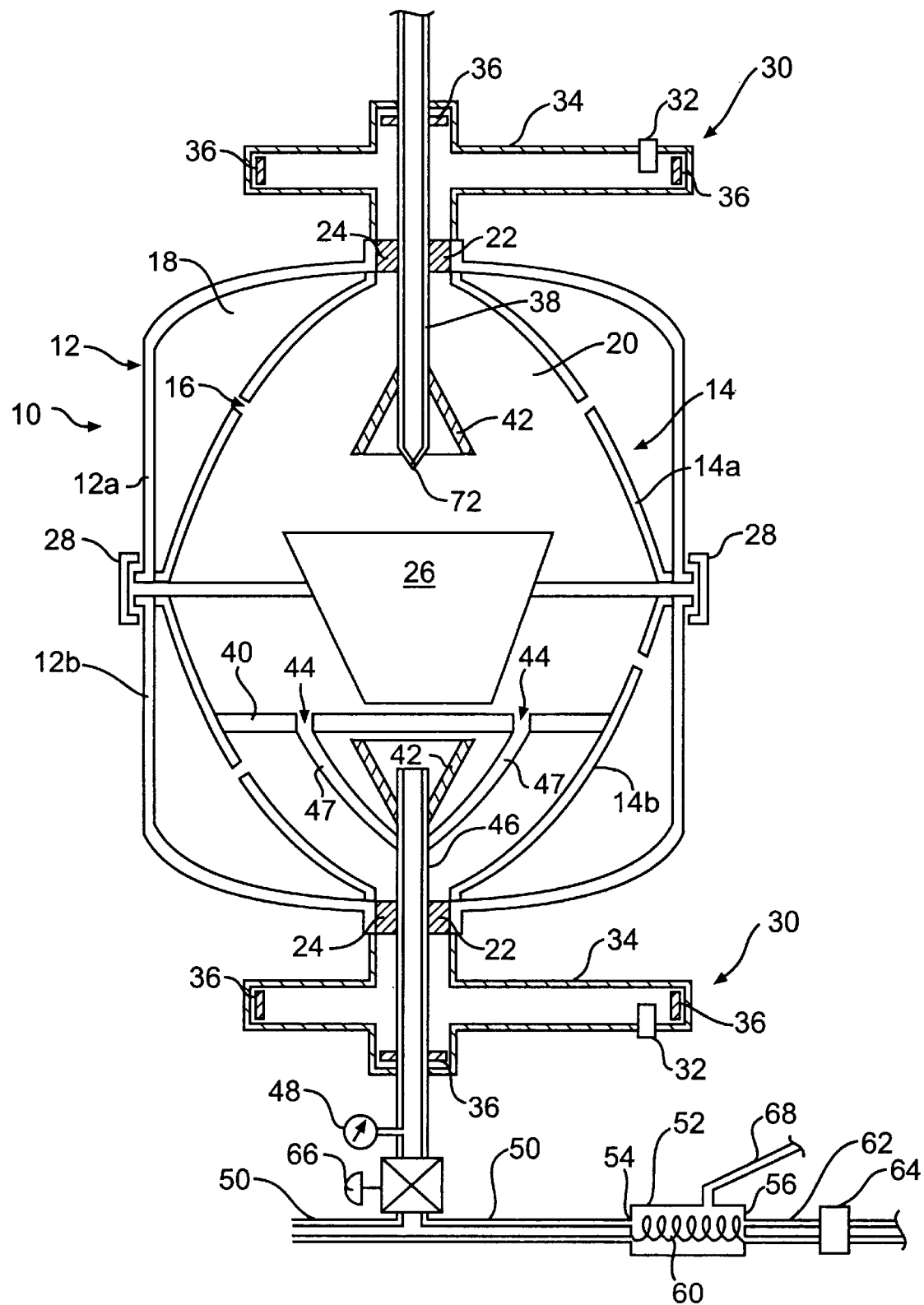
FIG. 1 is a simple cross sectional view of the components of one embodiment of the apparatus of the present invention.

Referring now in detail to the drawings and particularly to FIG. 1, there is shown an apparatus that is useful for the generation of steam and pressure by microwave energy.

The apparatus, comprising microwave pressure vessel 10, has a pressure hull (shell) 12 defining a volume. The hull 12 has upper and lower portions, 12a and 12b respectively, which are movable with respect to one another such that the hull 12 may be opened and closed. Within hull 12 is a liner 14, which, in the preferred embodiment, has two portions 14a and 14b attached to hull portions 12a and 12b, respectively. Openings or passageways 16 are provided in the liner 14 to provide communication between the space or volume 18 located between the liner 14 and the hull 12. The liner 14 preferably has a predetermined shape to improve efficiency and to focus the microwave energy as will be discussed below. While the liner 14 is preferred, it is not necessary, The pressure hull 12 may be used alone since it may be of any shape including the predetermined shape of the liner 14. However, manufacture of a pressure hull in the predetermined shape of the liner is expensive. Thus, it is preferred to use a hull of standard pressure vessel type and to attach thereto a liner of predetermined shape to promote the highest efficiency. Suitable latches (clamps) 28 are provided to hold the upper hull 12a and the lower hull 12b together so that pressure can be contained within the vessel 10.

The hull 12 or liner 14 defines a treatment chamber 20 adapted to receive a container 26, which is substantially transparent to microwave energy, for holding materials, objects, liquids and the like. Operatively associated with the hull 12 is a microwave generating assembly 30 for generating and transmitting microwaves into the treatment chamber 20. A controller 88 (FIG. 3) can be provided for regulating the source of microwaves. The apparatus of the invention is configured for the coaxial transmission of microwaves into the treatment chamber 20 and their single mode distribution into the material to be treated. Preferably, the pressure vessel uses liner 14 to aid in the formation, transmission and utilization of coaxial microwaves in the treatment chamber 20 and their single mode distribution into the chamber where they impinge on the material to be treated.

Preferably, the apparatus comprises a treatment chamber 20 defined by an upper hull 12a and a lower hull 12b, which, when sealed, form a cylindrical body that narrows, preferably in a parabolic arch, to a cylindrical neck 22 at either end of the apparatus. As illustrated in FIG. 1, the parabolic arch is configured from the liner 14. The openings of the necks are sealed with a material capable of acting as a barrier seal to contain pressure and steam, yet which is substantially transparent to microwaves, i.e., a material which allows microwave energy to pass through with acceptable loss. Preferably, the necks are sealed with a polytetrafluoroethylene Teflon dielectric disk 24 of sufficient thickness to contain the desired amount of pressure. A Teflon disk of about 1 inch in thickness has been found sufficient to contain pressures up to a minimum of 30 pounds per square inch.

Operatively associated with the neck of the upper hull 12a is a microwave generating waveguide assembly 30 communicating with the treatment chamber 20. This waveguide assembly comprises a microwave generator 32 and a waveguide 34. Preferably the microwave generator 32 is a magnetron capable of generating microwave energy. More preferably, it is a magnetron capable of operating at 2450 megahertz, a standard frequency which is readily available. The waveguide 34 comprises at least one rectangular waveguide section. In the preferred embodiment, arranged within the waveguide are tuning members 36 used to tune the microwaves to achieve maximum output. Most preferably, three tuning members 36 are provided.

Figure 2A:
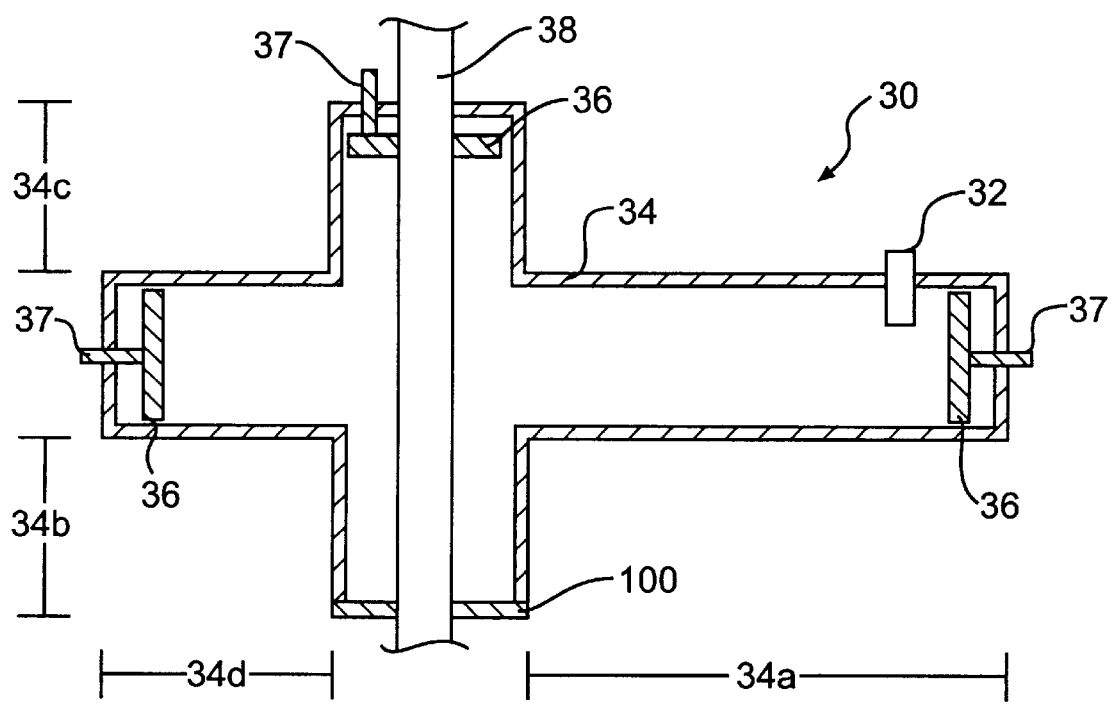
FIG. 2a is an isolated cross-sectional view of the coaxial microwave generating assembly.

Referring now to FIG. 2, the preferred microwave generating assembly is shown (like numbers in the drawings refer to like elements). The waveguide 34 is "t" shaped and has a main waveguide section 34a with the microwave generator 32 adjacent to the first end. At the second end of the main waveguide section are an output waveguide section 34b having an axis perpendicular to the axis of the main waveguide section and a first reflective waveguide section 34c positioned at the second end of the main waveguide 34a opposite to and coaxial with the output waveguide 34b. A second reflective waveguide section 34d, positioned adjacent to the first reflective waveguide section 34c and output waveguide section 34b, is coaxial with main waveguide section 34a. Linear member 38 (described below) passes through the waveguide coaxially with the axis of the output waveguide section 34b.

Figure 2B:
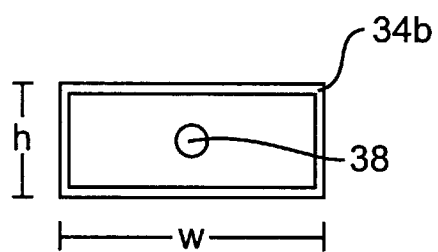
FIG. 2b is an end view of a waveguide section.

Each waveguide section preferably has the same cross section. The waveguide cross section is preferably selected such that one dimension "w" is the length of a full wave and another dimension "h" is the length of half a wavelength, as shown in FIG. 2b. The exact dimensions of the waveguide sections depend on the wavelength of the microwaves utilized. At a wavelength of 2450 megahertz the waveguide sections are preferably 4.46 inches in width and 2.31 inches in height.

Referring still to FIG. 2, an adjustable reflector or tuning member 36 is provided in the main waveguide section 34a, first reflective section 34c and second reflective section 34d. Each is provided with an adjustment device, such as a screw 37. Microwaves emitted from the generator 32 are propagated in both directions in the main waveguide 34a. Waves traveling toward the first end of the main waveguide section 34a impact on the reflector 36 and reflect back toward the linear element 38. The reflector 36 is adjusted such that the reflected waves are in harmony with waves originally propagated in the direction of the linear member 38. As the waves reach the linear member 38, some couple to it and travel coaxially along its length. Waves which do not couple with the linear member are reflected back toward the linear member by the reflector 36 in the second reflective waveguide section 34d. Waves which couple to the linear member 38 travel in both directions along the linear member 38 Those traveling away from the output waveguide section 34b are reflected back toward the output waveguide section 34b by the reflector 36 in the first reflective waveguide section 34c. The waveguide can be sealed with a Teflon dielectric disk 100 or other material transparent to microwaves.

Referring again to FIG. 1, traversing the waveguide 34 of the microwave generating assembly 30 and seal 24 of the upper hull 12a and projecting into the treatment chamber 20 is a linear member 38 capable of the coaxial transmission of microwaves as described above into the treatment chamber 20. Connected near the lower apical end of the linear member 38 is a conically shaped member 42. The tuning members or reflectors 36 are positioned such that they focus the microwaves emitted by the microwave generator 32 onto linear member 38 where the waves associate (or couple) with the linear member 38 in a coaxial fashion and are propagated through the sealing disk 24 into the treatment chamber 20 in a coaxial fashion along the length of the linear member 38.

Secured to the lower hull 12b defining the treatment chamber is a floor member 40. Preferably the floor member 40 is a disk substantially transparent to microwaves pierced by a plurality of vents 44 that communicate with drain conduits 47 which are connected to an outlet conduit 46 located beneath the floor member 40 and traversing the seal 24 of the cylindrical neck 22 of the lower hull 12b. Located within the outlet conduit 46 is a sensor 48 capable of measuring the pressure within the treatment chamber 20. In one embodiment, the sensor 48 may be implemented using, for example, a pressure transducer made by Ashcroft, Model No. ASH-K1-7-M02-42-F2. To contain the pressure and steam within the treatment chamber 20, a valve 66 is attached to the outlet conduit 46.

In addition, to remove particulates that may contaminate the valve 66 and the outlet conduits beyond, a filter structure (not shown) may be incorporated along the outlet conduit 46 between the lower outlet of the second microwave generating assembly 30 and the sensor 48. On implementation for such filter structure is a Cuno filter housing, Model No. CT101 (44153-01).

Figure 3:
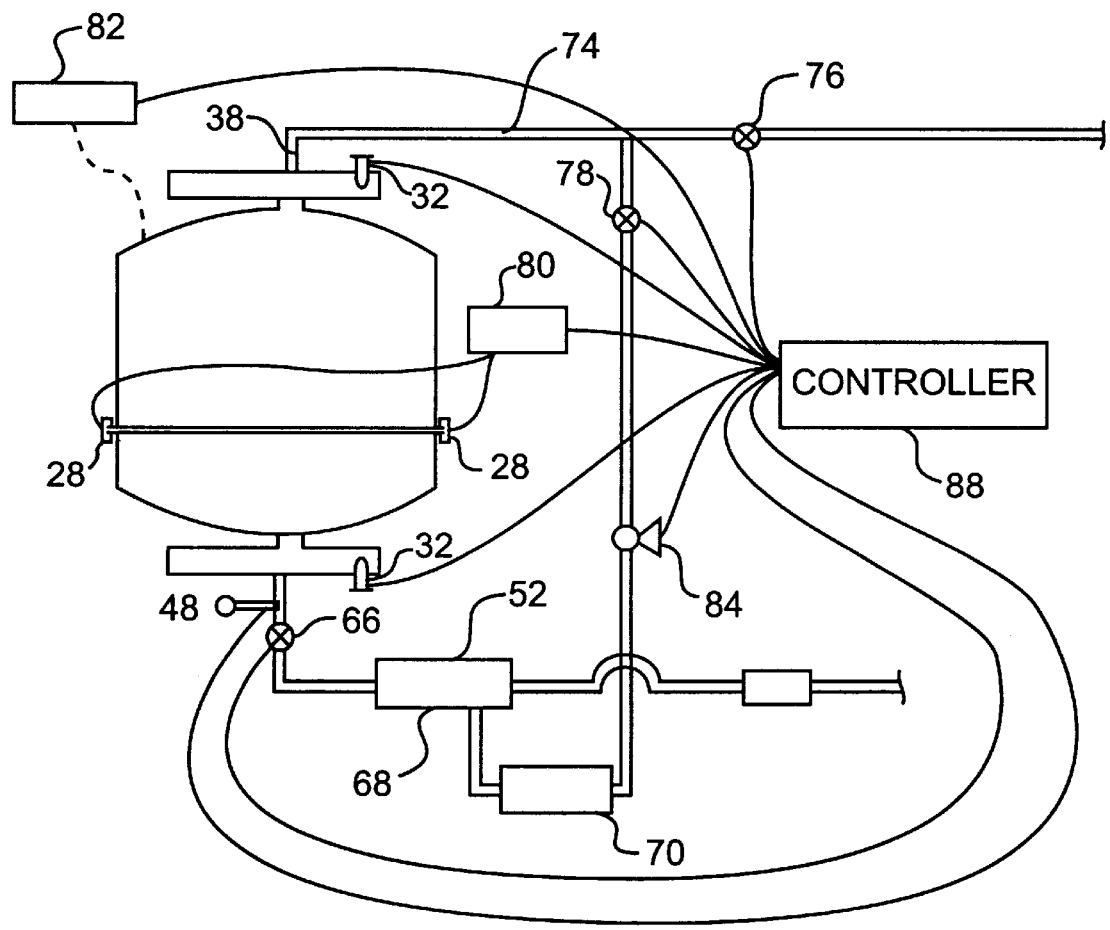
FIG. 3 is a schematic showing the relationship between the microwave Le pressure vessel and the remaining components of the present invention.

Referring to FIG. 3, the sensor 48 and valve 66 are operatively connected to a controller 88 capable of evaluating the signal generated by the sensor 48 and, in response thereto, regulating the release of steam and pressure from the treatment chamber 20. The controller can also be operatively connected to the microwave generator(s) 32 and can regulate the microwave generator in response to the signal received from the sensor 48. As a backup to the sensor 48, another pressure sensor or mechanical gauge (not shown) may be incorporated into the linear member 38 to measure the pressure at the nozzle 72, which is also indicative of the pressure in the treatment chamber 20.

Referring again to FIG. 1, preferably, the outlet conduit 46, divides, after valve 66, into two or more secondary outlet conduits 50, each of which is attached, at its far end to a flash chamber 52. Preferably, the flash chamber 52 is a cylindrically shaped member having an input end 54, an output end 56, and a diameter significantly larger than the diameter of the secondary outlet conduit 50 so as to affect a rapid expansion and cooling of the vented steam. The flash chambers preferably are filled with a material 60, preferably stainless steel wool, capable of promoting condensation and thereby reducing the temperature of the vented gases. After the condensate has been removed, the gases exit the container at its output end 56 which is connected to an exhaust conduit 62 communicating with the environment. The gases are preferably passed through a filter 64 capable of trapping noxious gases, preferably a charcoal filter, before they are released into the atmosphere. Flash chamber 52 also has a condensate outlet 68 communicating with a storage chamber or holding tank 70. (See FIG. 3).

The microwave generating assembly 30, conically shaped member 42, pressure vessel 10, and the linear member 38 are configured such that the microwaves are transmitted into the treatment chamber 20 along the linear member 38 in a coaxial fashion, then along the outside of the conically shaped device 42 until they reach its periphery and then are transferred to the inside of the chamber.

In order to efficiently utilize the co-axial microwave energy moving along linear member 38, it is necessary to decouple that energy from the linear member 38 and to spread it out. The inventors, while not being bound to any theory of operation, believe that the conically shaped device 42 helps decouple the coaxial wave from the linear member 38 and cause it to widen out and travel coaxially into the chamber 20. It has been found that if conical member 42 is hollow, it operates better. It is also believed that the conical member 42 may be acting as a capacitor which, upon discharge, emits a broad, uniform, single-mode microwave field into the material to be treated. Thus, while a linear member 38 alone, without conical device 42, may be useful in chambers of small diameter, the cone 42 has been found to be useful in chambers with a diameter which is more than 10 diameters of the linear member. These elements, however, should be tuned for the particular shape of each individual unit. It has been determined that a parabolic reflector disposed about the linear member improves efficiency. The initial parabola shape can then resolve into a general cylindrical shape. As shown in FIG. 1 the appropriate configuration can be provided by the liner 14, or, alternatively, the pressure hull 12 may be shaped as desired and the liner deleted. The base of the cone should be in the vicinity of a plane passing through ends the narrower portion of the parabola.

Figure 4:
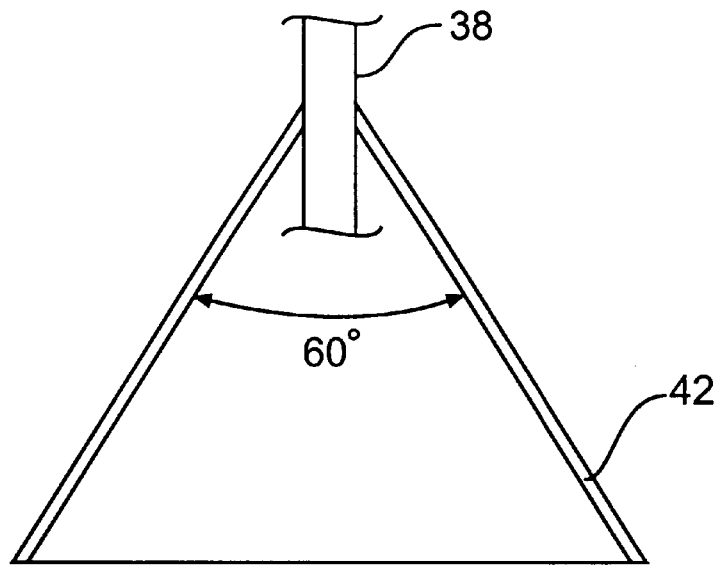
FIG. 4 is a simple cross sectional view of the conically shaped member.

It has been found that a ratio representing the base of the cone to the maximum diameter of the parabolic reflector can effectively be used in the range of about 1:3 to about 7:12. The angle forming the apex of the cone has been found to be useful between 30° and 90°. The length of the cone generally should be about 40% to 60% of the length of the parabola. Preferably the cone is an isosceles cone where the apex angle is 60° (See FIG. 4.) Much of the specific shapes and tuning for each individual vessel shape adopted is determined by experimentation. One can experimentally determine the shape of the microwave exiting the end of the linear member 38 by taking a number of shallow trays of Bisquick mix, placing them in the unit and then subjecting them to microwaves. The pattern of cooked and uncooked dough in each layer will allow one to visualize where the microwaves are being concentrated. One can determine the appropriate cone shape by observing the pattern of baking in the Bisquick mix. When the unit is suitably tuned, the Bisquick trays will exhibit concentric rings where material is more thoroughly baked with interposed rings of lesser baking.

In the preferred embodiment, associated with the neck 22 of the lower hull 12b is a second microwave generating assembly 30 communicating with the treatment chamber 20 and comprising a microwave generator 32 and a waveguide 34. Preferably, the second microwave generating assembly 30 is of the same type and construction as the upper microwave generating assembly.

Traversing the waveguide of the second microwave generating assembly 30 and the seal 24 of the lower hull 12b is the outlet conduit 46. Connected near its apical end is an inverted, conically shaped member 42. The tuning members or reflectors 36 of the second microwave generating assembly 30 are positioned such that they focus the microwaves emitted by the microwave generator 32 onto outlet conduit 46 whence the waves associate (or couple) with outlet conduit 46 and are propagated through the sealing disks 24 into the treatment chamber 20 in a co-axial fashion along the length of the outlet conduit 46. Drain conduits 47 are preferably made from a material substantially transparent to microwaves so as not to disrupt the energy pattern associated with outlet conduit 46.

The microwave generating assemblies 30, conically shaped members 42, pressure vessel 10, linear member 38 and the outlet conduit 46 are configured such that the microwaves are transmitted into the treatment chamber 20 along the linear member 38 and the outlet conduit 46 in a coaxial fashion, then along the outside of the conically shaped devices 42 until they reach their periphery and then are transferred to the inside of the chamber 20.

To maximize efficiency, it is preferred that the microwaves transferred into the treatment chamber 20 by the linear member 38 and outlet conduit 46 be non-interfering. Non-interfering microwave fields are achieved by tuning the waves as described above.

To generate steam, water can be added to the treatment chamber with the material, object, liquid or the like to be treated. Preferably, linear member 38 is a liquid injection conduit through which water or other liquids can be introduced into treatment chamber 20. Preferably, the water is sprayed into the chamber 20 by nozzle 72 located at the lower apical end of the liquid injection conduit (linear member 38).

Referring now to FIG. 3, water is supplied to the liquid injection conduit 38 by a water inlet conduit 74. The water supplied to the liquid injector unit is regulated by a valve 76 located between the liquid injector unit 38 and a conventional source of water (not shown). An additional source of water is the condensate located in holding tank 70. Preferably, holding tank 70 is in fluid communication with the water inlet conduit 74. Water is recycled by moving it from the holding tank to the water inlet conduit 74 by a pump 84. Located between the holding tank and water inlet conduit is a valve 78 for regulating the flow of recycled water into the water inlet conduit. In the sterilization of medical wastes, water is injected into the path of the microwaves to generate steam and heat until a pressure of about 22 psi (gauge) is reached as measured by the pressure sensor 48 located within outlet conduit 46.

To efficiently generate steam in those applications where steam is desired, water should be sprayed into the path of the microwaves such that the water is heated and flashed to steam. The heating is affected by the amount of water added, the length of the spray duration and the interval between water injection. By plotting pressure and temperature against time for various cone configurations one can determine the cone angle that achieves the best heating. By varying the length of each injection and the interval between injection, one can determine the optimum conditions for injection. It has been found that the injection of about 5 cups of water by injection for about 5 seconds 10 times over 10 minutes gives good results for the preferred embodiment described below.

It has also been found that the path of the injected water is important to achieve optimum heating and steam generation. It is important to disperse the injected water into the path of the microwaves such that the water is heated and vaporized to steam. This can be easily done experimentally by selecting different spray nozzles and varying the spray pattern in the apparatus. Spray nozzles are available which will emit sprays having different spray angles. By plotting the pressure and temperature against time, one can determine the most efficient spray pattern for a particular unit simply by testing a variety of nozzles and spray shapes. It has been found that a spray angle of between about 60° to 135° is useful. In the preferred embodiment, the spray angle is about 120°.

The sensor 48 is operatively connected to a controller 88 capable of evaluating the signal generated by the sensor. The controller 88 is further operatively connected to the microwave generators 32 and valves 66, 76, and 78, and capable of regulating them in response to the signal from the sensor. The controller is also connected to pump 84, and motors 80 and 82. Motor 82 is connected to an apparatus (not shown) to raise and lower the upper portion of the pressure vessel. Motor 80 drives the mechanism to operate clamping latches 28. Any conventional means to raise and lower the pressure hull 12 and to engage and disengage the latches 28 may be employed. Although the unit may be operated manually, it is preferred that it be controlled by the controller 88 which has been programmed to coordinate the functioning of the unit.

Processing starts with the vessel open. Waste is placed in the vessel preferably within waste container 26. Once the apparatus is started the controller initiates first motor 82 to lower the top of the vessel to the closed position and then motor 80 to close latches 28. The controller then closes valve 66, opens valve 78 and/or valve 76, and activates pump 84 and the microwave generator(s) 32. Further operation of valve 78 and/or valve 76, and pump 84 is preferably controlled by the program in the controller.

The controller receives the pressure signal, which is correlated to the temperature within the vessel 10, from sensor 48 and compares that signal to a pressure set point. Thus, the setpoint pressure is selected on the temperature desired within the vessel. One may also add a temperature monitor if so desired. Since the pressure measured is gauge psi pressure, at different altitudes different gauge pressures may be required to achieve the same temperature within the vessel. Generally, it has been found that when the atmospheric pressure is around 14.7 that a gauge pressure of 22 psi will correspond to a temperature in the range of about 268° F. to about 275° F. in the vessel. This temperature is sufficient to achieve'sterilization in the preferred embodiment. After comparing the pressure signal to the setpoint, the controller 88 opens the water supply and turns on the microwave generator(s) 32. Preferably, the initial water is supplied from reservoir 70. Once reservoir 70 is emptied, the controller preferably shuts down pump 84, closes valve 78 and then opens valve 76.

In the event that the pressure exceeds the setpoint the controller 88 then shuts off the water supply and deactivates the microwave generator(s) 32. Where the water is added by means of the liquid injection conduit 38, a final injection of water may be provided by the controller 88 to slightly cool the load before the water supply is cut off. In the preferred embodiment, exceeding the set pressure initiates a timer. The controller 88 continues to monitor the pressure in the vessel and maintains it at a level greater than or equal to the setpoint by initiating and terminating additional injections of water and activating and inactivating the microwave generators 32 as needed. After the desired time has elapsed, the controller shuts off the water supply and the microwaves and interrupts the comparator circuit.

The controller then opens the valve 66 permitting the steam and gases to exhaust from the vessel. Pressure is continually monitored and once it reaches a set pressure, the vessel may be open. Motor 80 is activated opening latches 28 and thereafter motor 82 is activated to open the pressure vessel.

Figure 6:
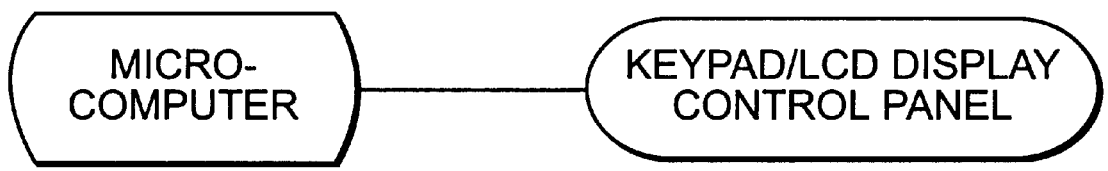
FIG. 6 is an electrical block diagram of the preferred controller.
Figure 5:
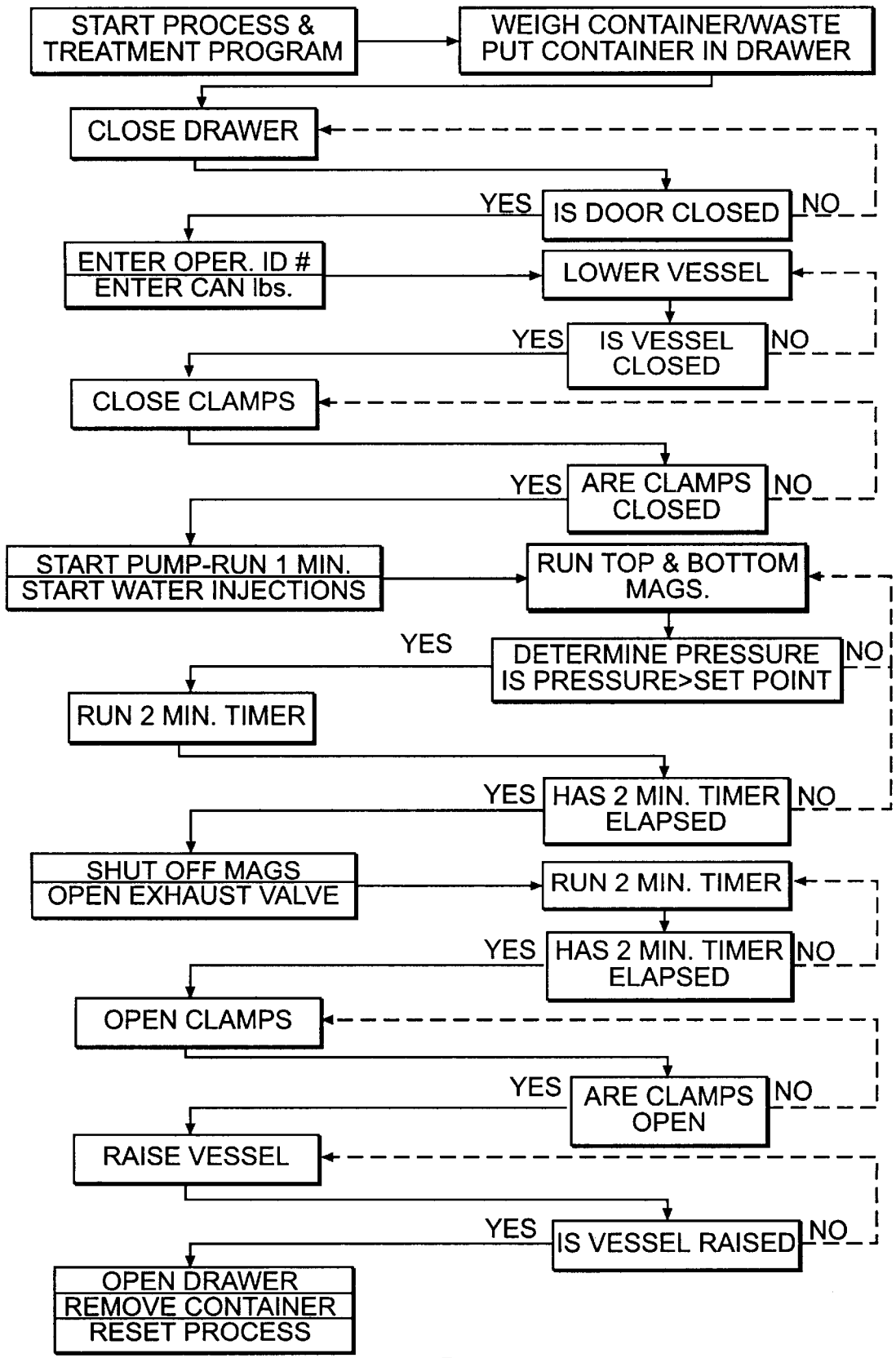
FIG. 5 is a flow chart illustrating the operation of the present invention.

The controller, illustrated in FIG. 6, is preferably a microcomputer and can be, for example, a Programmable Logic Computer (PLC), model 61200-A120, manufactured by Telemecanique. Operator access to the PLC and the controls of the microwave heating system is through a control panel, illustrated in FIG. 7, which consists of an Operator Interface Unit with an LCD screen, 10 functions keys and a numeric keypad. The present invention also relates to a process for heating under pressure materials, objects, liquids and the like. In one aspect, the invention is a process for the sterilization of medical wastes. However, it will be apparent that the process is also suitable for a wide range of applications.

The process for sterilization of medical wastes involves:
(a) placing medical wastes within a pressure vessel tuned to transmit coaxial and single-mode microwaves;
(b) adding water to wet said medical wastes; and
(c) subjecting said medical wastes to microwave radiation sufficient to generate sufficient steam and pressure for a sufficient time to sterilize said medical wastes.

Alternatively, the medical wastes may be sterilized by:
(a) placing medical wastes within a pressure vessel tuned to transmit coaxial and single-mode microwaves;
(b) subjecting said medical wastes to microwave radiation; and
(c) injecting sufficient water into the path of the microwaves to generate sufficient steam and pressure for a sufficient time to sterilize said medical wastes.

A device of the present invention found to be useful has an overall length of about 4 feet, measured from the upper seal 24 to the lower seal 24 of the pressure vessel. The maximum diameter of the pressure vessel is about 2 feet, with the cone(s) having a base from about 8 to 10 inches in diameter. The base of the cones is about 11 to 12 inches from the seals.

In one embodiment of the invention, with reference to FIG. 8 through FIG. 25, there is provided a microwave waste sterilizing 102 for sterilizing items as diverse as infectious medical waste, contaminated food products and animal tissue. The microwave waste sterilizer comprises an upper outer shell 104, a lower outer shell 106, an upper means for guiding microwave energy 108 connected to the upper outer shell 104, a lower means for guiding microwave energy 110 connected to the lower outer shell 106, an upper means for dispersing microwave energy 112 connected to the upper means guiding microwave energy 108, a lower means for dispersing microwave energy 114 connected to the lower means for guiding microwave energy 110, and a clamp 116 releasably holding the upper outer shell 104 and the lower outer shell 106 together.

Figure 13:
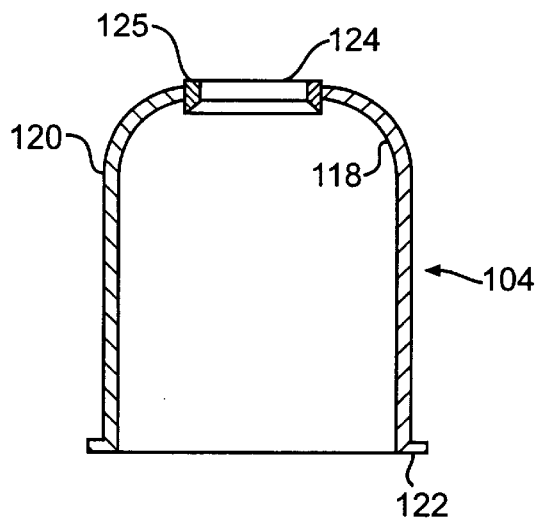
FIG. 13 is a cross-sectional view of the upper outer shell.
Figure 14:
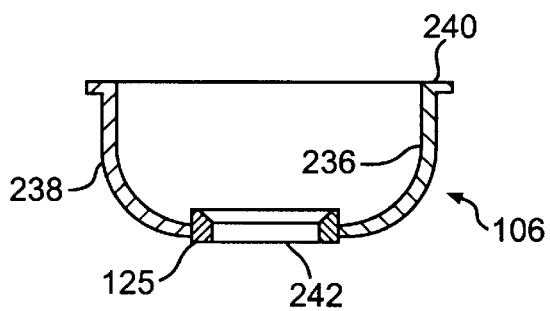
FIG. 14 is a cross-sectional view of the lower outer shell.

The upper outer shell 104, shown in FIG. 13, is generally bell shaped and has an inside surface 118, an outside surface 120, a flanged bottom end 122, a longitudinal axis, and a hole 124 at the apex of the bell shape. The hole 124 is coaxial with the longitudinal axis. The mating lower outer shell 106, shown in FIG. 14, is generally bowl shaped and has an inside surface 23b, an outside surface 238, a flanged top end 240, a longitudinal axis, and a hole 242 at an apex of the bowl shape. This hole 242 is coaxial with the longitudinal axis of the lower outer shell. The flanged ends of the upper and lower outer shells are designed to be held together by the clamp 116 to form a pressure vessel.

FIG. 9 shows the upper means for guiding microwave energy 108 which comprises an upper coaxial tube (linear element) 126 having an outside surface 128, a first end, a second end 130, an outside diameter, and a longitudinal axis, a substantially rectangular box shaped upper waveguide, a magnetron 152, a tubular first upper coax 154, a tubular upper conductor plug 160, a tubular second upper coax 162, a substantially can shaped upper z-neck 170, a tubular upper dielectric disc 184, and a funnel shaped conic support 192.

Figure 15:
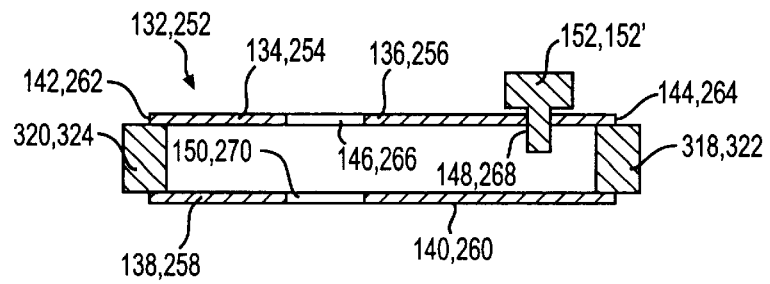
FIG. 15 is a cross-sectional view of another embodiment of the waveguide and magnetron.

As shown in FIG. 15, the upper waveguide 132 is a box which has a top plate 134 having an outside surface 136 and a bottom plate 138 having an outside surface 140. The top plate 134 has a first end 142, a second end 144, a first hole 146 between the first end 142 and a center of the top plate, and a second hole 148 near the second end 144. The second hole has a diameter smaller than a diameter of the first hole 142. The bottom plate 138 is substantially parallel to the top plate 134 and has a hole 150 of a diameter substantially the same as the diameter of the first hole 146 in the top plate 134. The hole 150 in the bottom plate 138 is oriented in axial alignment with the first hole 146 in the top plate 134. The magnetron 152 is connected to the top plate 134 of the upper waveguide 132 at the second hole 148 so that waves produced by the magnetron 152 are broadcast within the rectangular box shaped upper waveguide. A magnetron identical to one used in a standard household microwave may be successfully used. Magnetrons varying in power ratings from 300 watts to 3000 watts have been installed; however, a 1400-watt magnetron, such as model 2MI21A-53 from Richardson Electronics Ltd., has been used with good results. In a preferred embodiment, the upper wave guide 112 also has a first movable end block (tuning member) 318 and a second movable end block (tuning member) 320. Each movable end block has the characteristic of a tuning short to help tune the microwaves being broadcast.

The first upper coax 154 (FIG. 1) has a first end 156, a second end 158, an inside surface defining a diameter substantially the same as the diameter of the first hole 146 in the top plate 134 of the upper waveguide 132, and a longitudinal axis. The first end 156 is connected to the outside surface 136 of the top plate 134 so that the longitudinal axis is coaxial with the first hole 146 and the first upper coax 154 is in covering relationship to the first hole 146. A welded connection has proved successful, although other attachment means could be used. The upper conductor plug 160 has a first end, a second end, an outside diameter substantially the same as the inside diameter of the first upper coax 154, an inside surface defining a diameter substantially the same as the outside diameter of the upper coaxial tube 126, and a longitudinal axis. The upper conductor plug 160 is closely received by the second end 158 of the first upper coax 154. In a preferred embodiment, the upper plug may be adjusted up and down within the first coax, thus allowing the conductor plug to function as a tuning short. The first upper coax and upper conductor plug help direct and turn the microwave energy from the upper waveguide to the upper coaxial tube.

Figure 16:
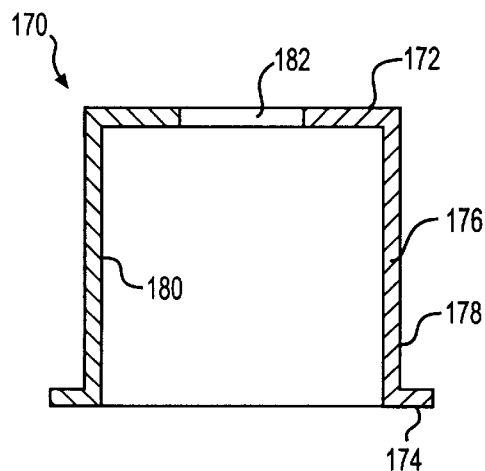
FIG. 16 is a cross-sectional view of the upper z-neck.
Figure 17:
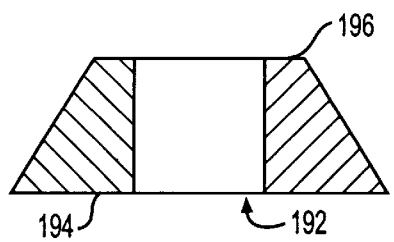
FIG. 17 is a cross-sectional view of a conic support.
Figure 18:
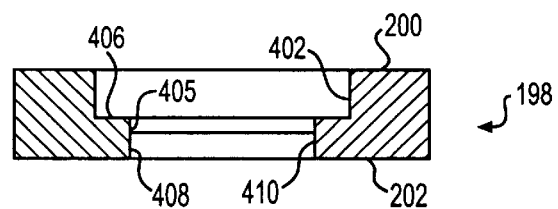
FIG. 18 is a cross-sectional view of a collar.

The second upper coax 162 (FIG. 11) has a first end 164, a flange end 166, an inside surface 168 having a diameter substantially the same as the diameter of the hole 150 in the bottom plate 138 of the upper waveguide 132, and a longitudinal axis. The flange end 166 is substantially ring shaped and has a generally cylindrical inside surface coincident with the inside surface 168 of the second upper coax 162. The first end 164 is connected to the outside surface 140 of the bottom plate 138 so that the longitudinal axis is coaxial with the hole 150 and the second upper coax 162 is in covering relationship to the hole 150. A welded connection has proved effective FIG. 16 shows the upper z-neck 170 which has a top end 172, a flange end 174, a generally tubular sidewall 176 having an outside surface 178 connecting the top end 172 and the flanged end 174 and an inside surface 180 having a diameter greater than the diameter of the second upper coax 162, and a longitudinal axis. The top end 172 has a hole 182 coaxial with the longitudinal axis. This hole 182 has a diameter substantially the same as the diameter of the inside surface 168 of the second upper coax 162. The flange end 174 is substantially ring shaped and has a generally cylindrical inside surface coincident with the inside surface 180 of the upper z-neck 170. The top end 172 is connected to the flange end 166 of the second upper coax 162. A bolted attachment has proved successful. The flange end 174 is connected to the outside surface 120 (FIG. 13) of the upper outer shell 104 in covering relationship to the hole 124 in the apex of the upper outer shell 104. Again, a bolted attachment has proved successful. The upper z-neck and second upper coax help to direct the microwave energy towards the upper means for dispersing microwave energy.

The upper dielectric disc 184 (FIG. 9) has a first end 186, a second end 188, an outside diameter, a longitudinal axis, and an inside surface defining a diameter 190 substantially the same as the outside diameter of the upper coaxial tube 126. The conic support, shown in FIG. 17, has an inside surface defining a diameter substantially the same as the outside diameter of the upper coaxial tube 126, a top surface 194 which has an outside diameter smaller than the outside diameter of the upper dielectric disc 184, a bottom surface 196 which has an outside diameter smaller than the outside diameter of the top surface 194, and a longitudinal axis. The top surface 194 is connected to the second end 188 of the upper dielectric disc 184 by use of an adhesive such as silicon chalk. The upper dielectric disc 184 and the conic support 192 need to have the characteristic of being substantially transparent to microwaves, thus functioning as windows. It has been found that virgin polytetrafluoroethylene works well with the type of microwaves being broadcast.

Figure 11:
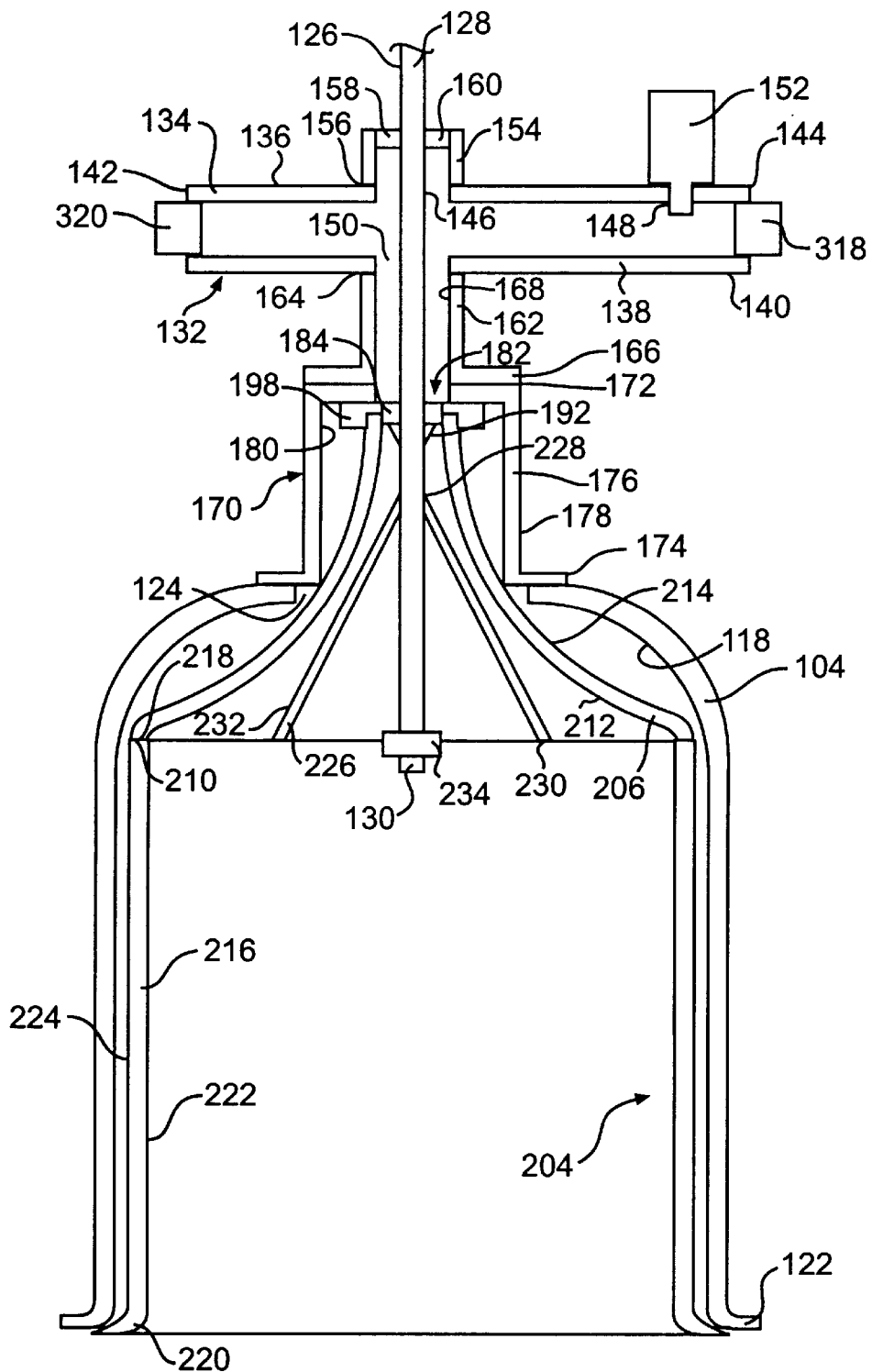
FIG. 11 is a cross-sectional view of the upper sections as assembled.

The longitudinal axes of the upper shell 104, upper coaxial tube 126, first upper coax 154, upper conductor plug 160, second upper coax 162, upper z-neck 170, dielectric disc 184, and conic support 192 are all coaxial. Further, the upper coaxial tube 126 extends through the upper conductor plug 160, first upper coax 154, upper waveguide 132, second upper coax 162, upper z-neck 170, upper dielectric disc 184 and conic support 192 (FIG. 11).

The upper coaxial tube, upper waveguide, first upper coax, upper conductor plug, second upper coax, and upper z-neck are made from a microwave reflective material, such as silver, nickel or aluminum. Aluminum is preferred for ease of fabrication and cost.

The upper means for dispersing microwave energy 112, also shown in FIG. 9, comprises a generally ring-shaped collar 198, an upper liner 104, a hollow deflection cone 226, and a tubular upper deflector collar 234. The collar, shown in FIG. 18, has a first end 200, a second end 202, an outside diameter, a first generally cylindrical inside surface 402 having a first inside diameter adjacent to the first end 200, a second generally cylindrical inside surface 404 having a second inside diameter which is smaller than the first inside diameter, a first annular shoulder 406 joining the first generally cylindrical surface 402 with the second generally cylindrical 404 surface, a third generally frustoconically shaped inside surface 408 adjacent to the second end and converging from the second end 202 toward a longitudinal axis of the collar 198 at an angle of about 5°, and a second annular shoulder 410 joining the second generally cylindrical surface 404 with the third generally frustoconically shaped inside 408. The first inside diameter is substantially the same as the outside diameter of the upper dielectric disc 184 so as to closely receive the upper dielectric disc 184. The second inside diameter (FIG. 16) is substantially the same as the diameter of the hole 182 in the top end 172 of the upper z-neck 170. The second inside diameter and the frustoconically shaped inside surface 408 are larger than the outside diameter of the conic support 192. The outside diameter of the collar is smaller than the diameter of the inside surface 180 of the upper z-neck 170 so that the upper dielectric disc 184, conic support 192 and collar 198 all nest within the upper z-neck 170 as shown in FIG. 9. The collar is preferably made from aluminum.

Figure 19:
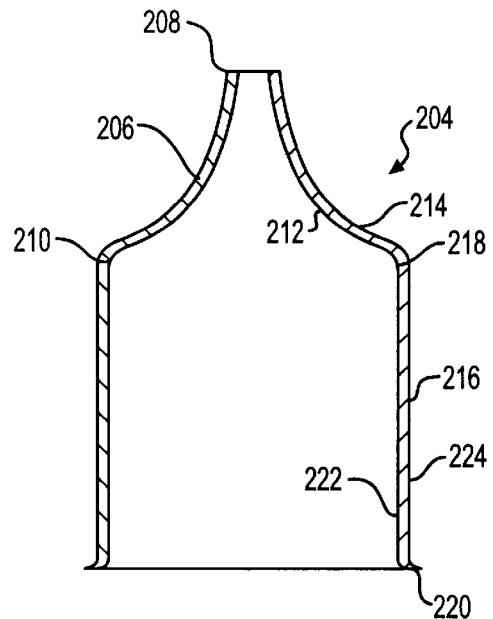
FIG. 19 is a cross-sectional view of an upper inner liner.
Figure 26:
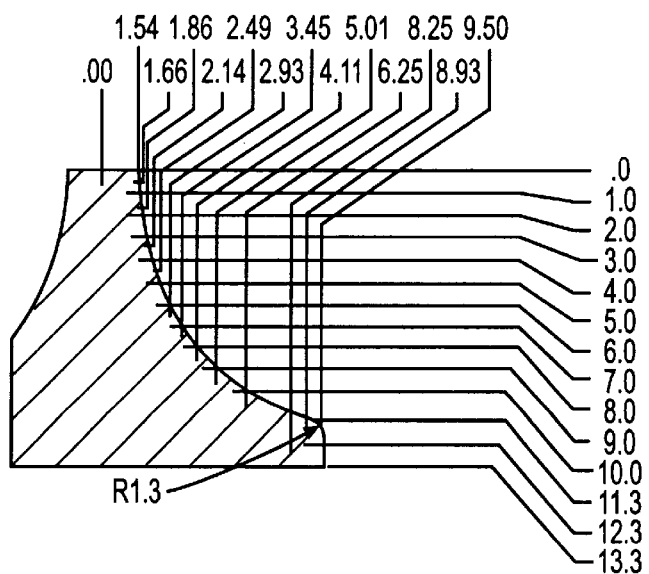
FIG. 26 is a sectional view of the inside surface of a parabolic shaped bell, depicting a curvature of the inside surface.

FIG. 19 shows the upper liner which has a longitudinal axis and comprises a parabolic-shaped bell portion 206 having a first end 208 having an inside diameter, a second end 210 having an inside diameter larger than the inside diameter of the first end 208, an inside surface 212, and an outside surface 214, and a tubular-shaped extension portion 216 having a first end 218 connected to the second end 210 of the parabolic-shaped bell portion 206, a second flanged end 220, an inside surface 222, and an outside surface 224. The parabolic shape depicted in FIG. 26 has been used with good results. The outside surface 214 of the parabolic-shaped bell portion 206 at the first end 208 is connected to the third generally frustoconically-shaped inside surface 408 (FIG. 18) of the collar such that the upper dielectric window is substantially on top of the bell portion in covering relationship to the first end and the conic support is within the bell portion at the first end. The second flanged end 220 (FIG. 19) of the extension portion 216 nests against the flanged bottom end 122 (FIG. 13) of the upper outer shell 104. The flanged end is designed to not only provide a pressure seal when the system is clamped together, but to provide an RF energy seal for the system. The outside surface 214, 224 of the parabolic-shaped bell portion 206 and the tubular-shaped extension portion 216 of the upper inner liner 204 are adjacent to the inside surface 118 of the upper outer shell 104 (FIG. 11). In a preferred embodiment, the upper liner is constructed from aluminum and the parabolic-shaped bell portion is formed by spinning. The parabolic-shaped bell portion and the extension portion may be made from a single piece, however, it has been found easier to fabricate the portions as separate parts and then weld them together.

Figure 20:
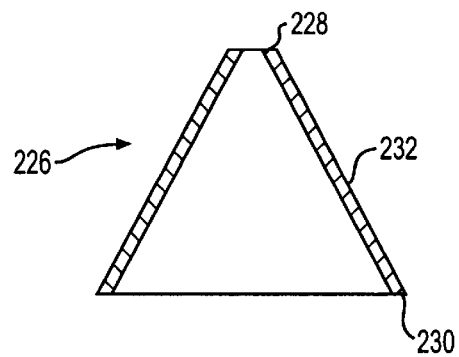
FIG. 20 is a cross-sectional view of a deflection cone.

The upper deflection cone 226, shown in FIG. 20, has a truncated first end 228, a second end 230, a longitudinal axis, and an outside surface 232 converging from the second end 230 towards the first end 228 at an angle between 45° and 55°. The truncated first end 228 has an inside diameter substantially the same as the outside diameter of the upper coaxial tube 126 and the cone is attached to the outside surface 128 of the upper coaxial tube 126 at the truncated first end 228 at a position between the collar 198 (FIG. 18) and the second end 230 of the deflector cone 226. A welded attachment has proven successful. It is preferred that the cone be placed in position such that the second end 230 and the bottom of the parabolic-shaped bell portion are contained in the same plane. The outside surface 232 (FIG. 11) of the deflection cone 226 is adjacent to the inside surface 212 of the parabolic-shaped bell portion 206. The deflection cone, like the upper liner, is preferably fabricated from aluminum.

The upper deflection collar, otherwise known as a "donut" has a first end, a second end, an outside diameter substantially smaller than a inside diameter of the second end 230 of the deflection cone 226, an inside surface having a diameter substantially the same as the outside diameter of the upper coaxial tube 126, and a longitudinal axis. The inside surface is connected to the upper coaxial tube 126 near the second end 130 of the upper coaxial tube 126 such that a plane which contains the second end 230 of the deflection cone 226 passes through the upper deflection collar normal to the longitudinal axis of the upper deflection collar. The upper deflector collar is preferably made from aluminum.

While not wishing to be bound to any theory of operation, it is believed that the microwave energy travels down the upper coaxial tube from the upper means for guiding microwave energy into the upper means for dispersing microwave energy, where it is split into three paths, the first being between the upper liner and the deflection cone. The second path is along the inside surface of the deflection cone and the third path is along the upper coaxial tube. The upper deflection collar acts to redirect energy which stands off the second end of the deflection cone. The waves are redirected into the inside of the deflection cone or to the parabolic-shaped bell portion of the upper liner.

The longitudinal axes of the upper outer shell 104, upper coaxial tube 126, collar 198, upper liner 204, deflection cone 226 and upper deflection collar 234 are coaxial. Further, the upper coaxial tube 126 extends through the collar 198, parabolic-shaped bell portion 206, deflection cone 226 and upper deflection collar 234.

Figure 7:
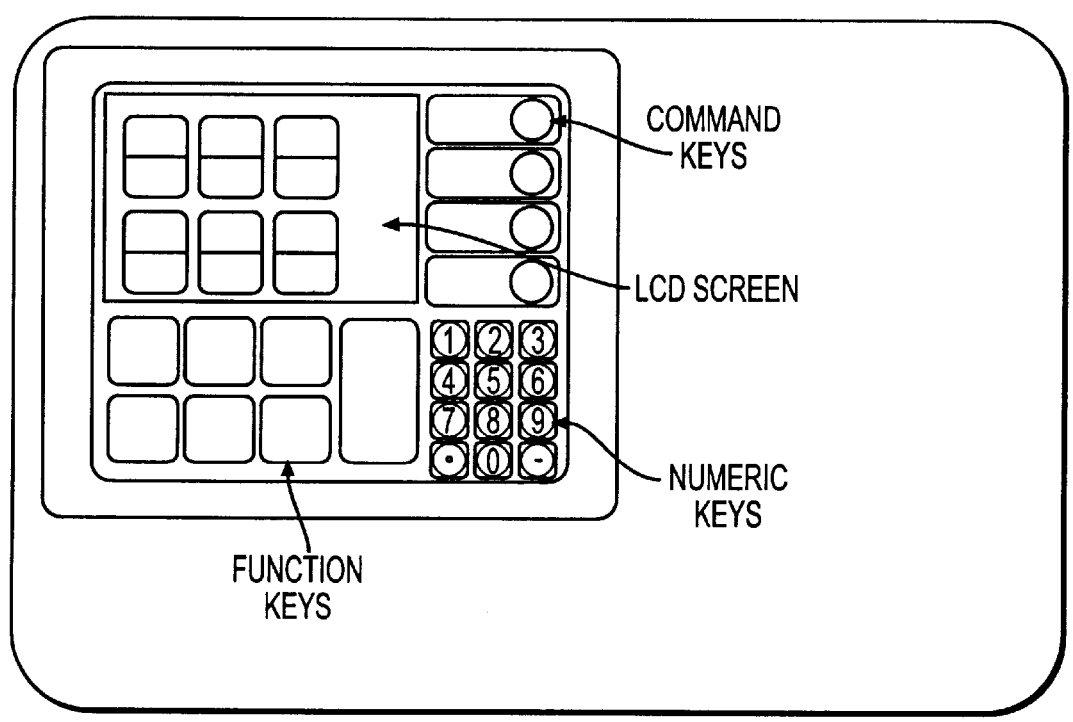
FIG. 7 is a diagram of the Operator Interface Unit.
Figure 8:
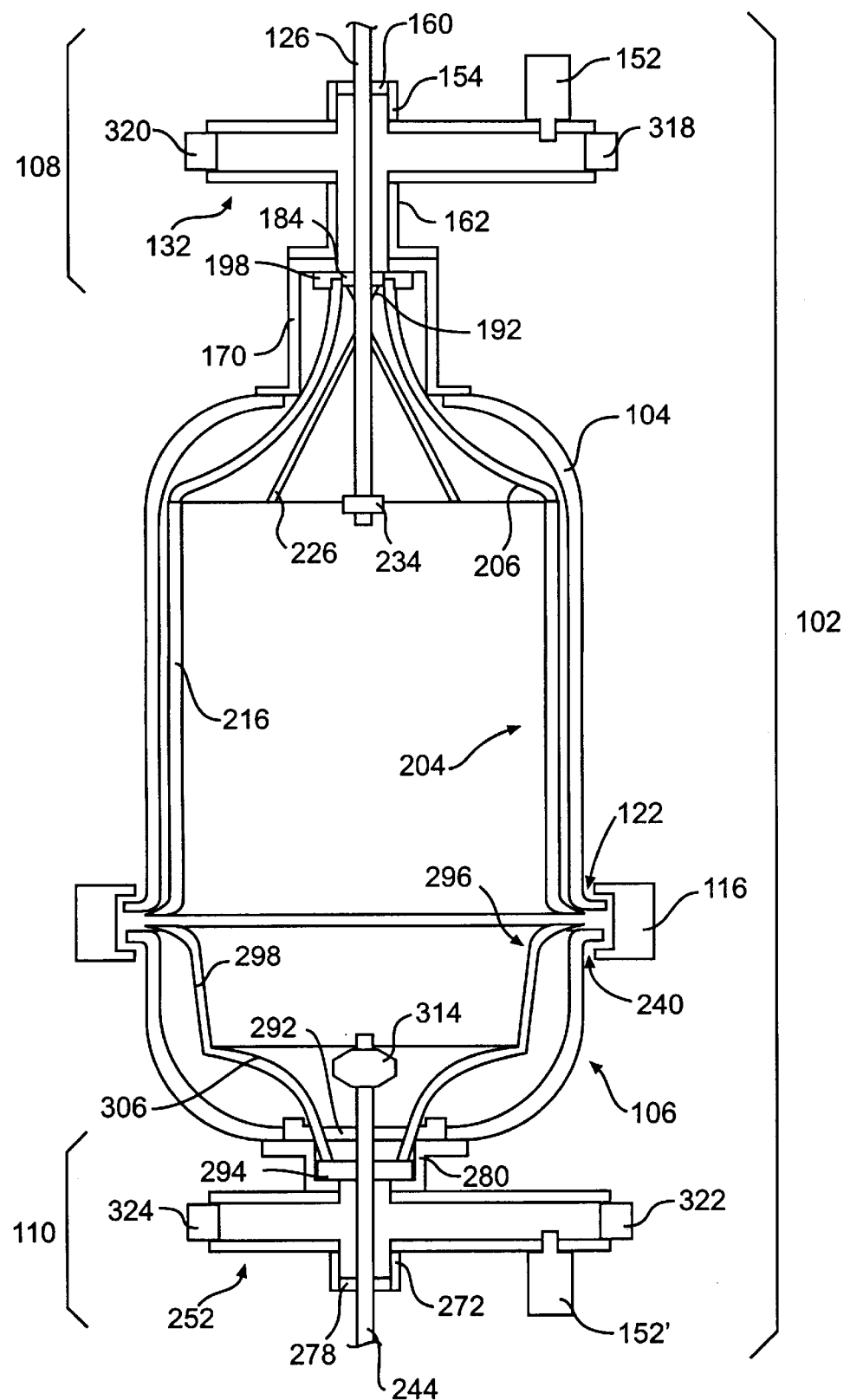
FIG. 8 is a cross-sectional view showing another embodiment of the sterilizer as assembled.
Figure 12:
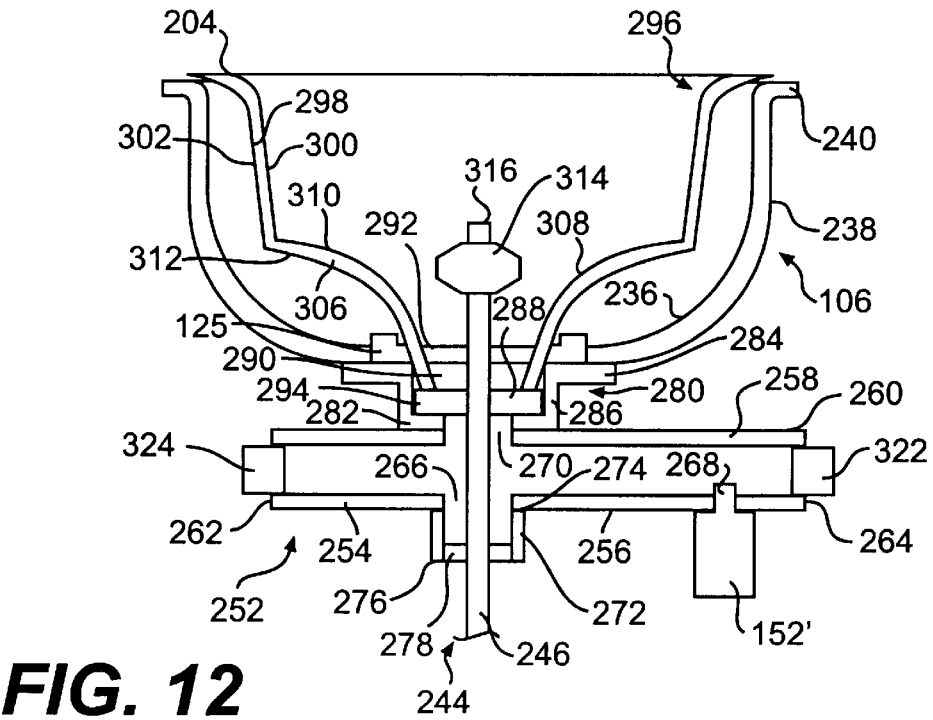
FIG. 12 is a cross-sectional view of the lower sections as assembled.

FIGS. 7, 10 and 12 show the lower means for guiding microwave energy 110. Similar to the upper means for guiding microwave energy, the lower means for guiding microwave energy comprises a lower coaxial tube 244 having an outside surface 246, a first end 248, a second end 250, an outside diameter, and a longitudinal axis, a substantially rectangular box-shaped lower waveguide 252, a magnetron 152', a tubular lower coax 272, a tubular lower conductor plug 278, a substantially can-shaped lower z-neck 280, and a generally tubular lower dielectric disc 292.

The lower waveguide 252, shown in FIG. 15, is comparable to that described for the upper waveguide, only upside down. There is a top plate 258 having an outside surface 260 and a bottom plate 254 having an outside surface 256. The bottom plate 254 has a first end 262, a second end 264, a first hole 266 between the first end 262 and a center of the bottom plate and a second hole 268 near the second end 264. The second hole has a diameter smaller than the o.10 first hole 266. The top plate 258 is substantially parallel to the bottom plate 254 and has a hole 270 of a diameter substantially the same as the diameter of the first hole 266 in the bottom plate 254. This hole 270 in the top plate 258 is in axial alignment with the first hole 266 in the bottom plate 254. A magnetron 152' is connected to the bottom plate 254 of the lower waveguide 252 at the second hole 268 so that waves produced by the magnetron 152' are broadcast within the rectangular box-shaped lower waveguide 252. The lower magnetron is similar to the upper magnetron. When energized, the upper and lower magnetrons are set to broadcast at 180°, minimus of 120°, out of phase with each other. In a preferred embodiment the lower wave guide 252 also has a first movable end block 322 and a second movable end block 324. Each movable end block functions as a tuning short.

The lower coax 272 (FIGS. 10, 12 and 15) has a first end 274, a second end 276, an inside surface defining a diameter substantially the same as the diameter of the first hole 266 in the bottom plate 254 of the lower waveguide 252, and a longitudinal axis. The first end 272 is connected to the outside surface 256 of the bottom plate 254 so that the longitudinal axis is coaxial with the first hole 266 and the lower coax 272 is in covering relationship to the first hole 266. A plate may be attached to the first end to act as a stiffener. If used, the plate must have a hole substantially the same as the inside diameter of the lower coax. A lower conductor plug 278 is used in association with the lower coax. The conductor plug has a first end, a second end, an outside diameter substantially the same as the inside diameter of the lower coax 272, an inside surface defining a diameter substantially the same as the outside diameter of the lower coaxial tube 244, and a longitudinal axis. The lower conductor plug 278 is closely received by the second end 276 of the lower coax 272. In a preferred embodiment, the position of the lower conductor plug is adjustable within the lower coax so that the lower conductor plug functions as a tuning short. The lower coax and lower conductor plug help direct and turn the microwave energy from the lower waveguide to the lower coaxial tube.

Figure 21:
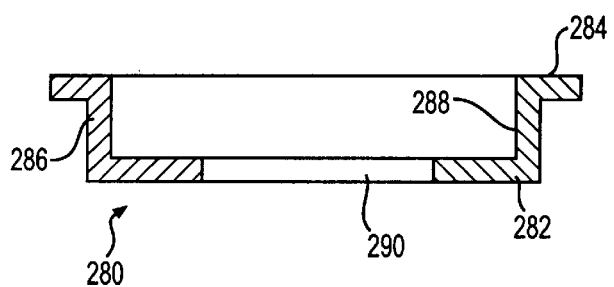
FIG. 21 is a cross-sectional view of a lower z-neck.

FIG. 21 shows the lower z-neck 280 which has a bottom end 282, a flange end 284, a generally tubular sidewall 286 having an outside surface connecting the bottom end 282 and the flanged end 284 and an inside surface 288 having a diameter greater than the diameter of the hole 270 in the top plate 258 of the lower waveguide 252, and a longitudinal axis. The bottom end 282 has a hole 290 coaxial with the longitudinal axis. The hole 290 has a diameter substantially the same as a diameter of the hole 270 in the top plate 258 of the lower waveguide 252. The flange end 284 is substantially ring-shaped and has a generally cylindrical inside surface coincident with the inside surface 288 of the lower z-neck 280. The bottom end 282 is connected to the top plate 258 of the lower waveguide 252 (FIG. 12) so that the hole 290 in the bottom end 282 is coaxial with the hole 270 in the top plate 258 and the bottom end 282 is in covering relationship with the hole 270. The flange end 284 is connected to the outside surface 238 of the lower outer shell 106 in covering relationship to the hole 242 in the apex of the bell shape of the lower outer shell 106. A plate may be used between the lower z-neck and the lower waveguide to act as a stiffener. If used, the plate must have a hole substantially the same as the hole in the top plate of the waveguide. The lower z-neck helps to direct the microwave energy towards the lower means for dispersing microwave energy.

Figure 22:
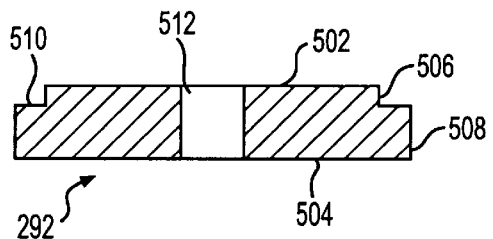
FIG. 22 is a cross-sectional view of a lower dielectric disc.
Figure 23:
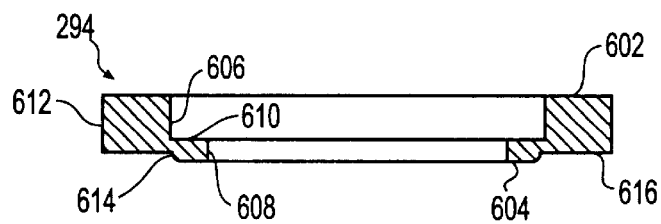
FIG. 23 is a cross-sectional view of an adaptor.

The lower dielectric disc 292, shown in FIG. 22, has a first end 502, a second end 504, a longitudinal axis, a first outside surface 506 adjacent to the first end 502 and having a first outside diameter, a second outside surface 508 adjacent to the second end 504 and having a second outside diameter which is greater than the first outside diameter, a first annular 510 joining the first outside surface 506 and the second outside surface 508 and an inside surface defining a diameter substantially the same as the outside diameter of the lower coaxial tube 244. The lower dielectric disc 292 is positioned in the lower z-neck 280 in covering relationship with the hole 290 in the bottom end 282 of the lower z-neck 280. The lower dielectric disc 292 has the characteristic of being substantially transparent to microwaves, thus functioning as a window. It has been found that virgin polytetrafluoroethylene functions well as the dielectric material.

The longitudinal axes of the lower outer shell 106, lower coaxial tube 244, lower coax 272, lower conductor plug 278, lower z-neck 280 and lower dielectric disc 292 are coaxial. Further the lower coaxial tube 244 extends through the lower conductor plug 278, lower coax 272, lower waveguide 252, lower z-neck 280 and lower dielectric disc 292 as shown in FIG. 12.

The lower waveguide, lower coaxial tube, lower coax, lower conductor plug, and lower z-neck are made from a microwave friendly material such as stainless steel, silver, nickel or aluminum. Aluminum is preferred for ease of fabrication and cost. Stainless steel is preferred for reflectivity and resistance to corrosion.

The lower means for dispersing microwave energy is shown in FIG. 12. The system comprises a generally tubular adaptor 294, a lower inner liner 296, and a lower deflector 314. The adaptor 294, shown in FIG. 23, has a first end 602, a second end 604, a first inside surface 606 adjacent to the first end 602 and having a first inside diameter, a second inside surface 608 adjacent to the second end 604 and having, a second inside diameter smaller than the first inside diameter, a first annular shoulder 610 joining the first inside surface 606 and the second inside surface 608, a first outside surface 612 adjacent to the first end 602 and having a first outside diameter, a second outside surface 614 adjacent to the second end 604 and having a second outside diameter smaller than the first outside diameter, a second annular shoulder 616 joining the first outside surface 612 and the second outside surface 614, and a longitudinal axis. The first inside diameter is substantially the same as the first outside diameter of the lower dielectric disc 292 so as to closely receive the lower dielectric disc 292. The second inside diameter is substantially the same as the diameter of the hole 290 in the bottom end 282 of the lower z-neck 280. The first outside diameter is smaller than the diameter of the inside surface 288 of the lower z-neck 280. This allows the lower dielectric disc 292 and the adapter 294 to nest within the lower z-neck 280. The adaptor is preferably made from aluminum.

Figure 24:
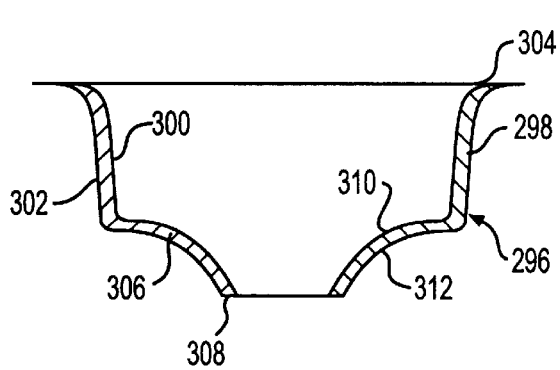
FIG. 24 is a cross-sectional view of a lower, inner liner.

FIG. 24 shows the lower liner 296 which is symmetric about a longitudinal axis and comprises a substantially tubular-shaped portion 298 and a parabolic-shaped bell portion 306 which is connected to the tubular-shaped portion at a point of transition. The tubular portion has an inside surface 300, an outside surface 302, and a flanged end 304. The parabolic-shaped bell portion has a first end 308 having an inside diameter smaller than an inside diameter of the tubular-shaped portion an inside surface 310 and an outside surface 312. The parabolic shape depicted in FIG. 26 has been used with good results. It has been found beneficial if the point of transition between the tubular portion and the parabolic-shaped bell portion is generally a sharp angle near to 90°. The outside surface 312 of the parabolic-shaped bell portion 306 at the first end 308 is closely received by the first inside surface 614 of the adaptor 294. The flanged end 304 of the tubular-shaped portion 298 nests against the flanged top end 240 of the lower outer shell 106. As in the upper inner liner, the flanged end is designed to not only provide a pressure seal when the system is together, but to provide an RF energy seal for the system. The outside surfaces 302, 312 of the tubular portion 298 and the parabolic-shaped bell portion 306 of the lower inner liner 296 are adjacent to the inside surface 236 of the lower outer shell 106. In a preferred embodiment, the lower inner liner is fabricated from aluminum and is formed by a spinning process. Lower and upper liners have a synergistic coating such as magna plate HRC.

Figure 25:
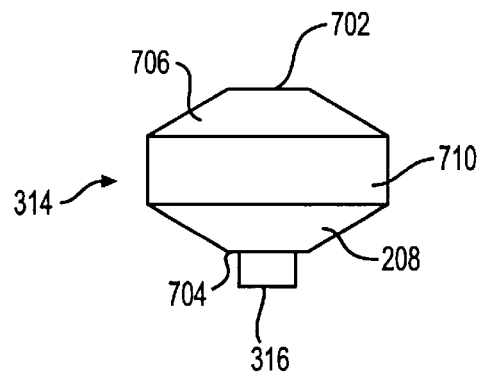
FIG. 25 is a cross-sectional view of a lower deflector.

The lower deflector 314, shown in FIG. 25, has a first end 702, a second end 704, a first generally frustoconically-shaped outside surface 706 adjacent to the first end 702, a second generally frustoconically-shaped outside surface 708 adjacent to the second end 704, a third generally cylindrical outside surface 710 connecting the first outside surface 706 and the second outside surface 708, and a longitudinal axis. The first frustoconically-shaped outside surface 706 converges away from the first end 702 at an angle of between about 8° and 25°. The second frustoconically-shaped outside surface 708 converges away from the second end 704 at an angle between about 8° and 25°, thereby substantially mirroring the first frustoconically-shaped outside surface 706. The first end 702 is connected to the second end 250 of the lower coaxial tube 244 such that a common plane passes through the lower deflector and the near 90 degree point of transition between the tubular portion 298 and the parabolic-shaped bell portion 306 of the lower inner liner 296. The lower deflector is preferably made from aluminum and also has a magna plate HRC coating.

The microwave energy travels up the lower coaxial tube from the lower means for guiding microwave energy into the lower means for dispersing microwave energy, where it is split into two paths, the first being between the liner and the deflector and the second path being along the lower coaxial tube. The lower deflector acts to redirect energy which stands off the near 90 degree point of transition between the tubular portion 298 and the parabolic-shaped bell portion 306 of the lower liner. The energy is redirected towards the parabolic shaped bell portion and a central area within the lower liner. A nipple 316 may be added to the second end 704 of the deflector 314 to further tune the microwave energy which stands off the inner liner at the near 90 degree point of transition between the tubular portion 298 and the parabolic-shaped bell portion 306. The nipple should be cylindrical with a longitudinal axis coaxial with the longitudinal axis of the deflector 314.

The longitudinal axes of the lower outer shell 106, lower coaxial tube 244, adaptor 294, lower inner liner 296 and deflector 314 are coaxial. Further, the lower coaxial tube 244 extends through the adapter 294, parabolic-shaped bell portion 306 of the inner liner 298 and deflector 314.

In a preferred embodiment, the microwave waste sterilizer 102 should also include a reusable plastic or fiberglass waste container, a disc-shaped support tray 316 positioned to support the waste container within the microwave waste sterilizer 102, a liner heater, and a means for external control. The support tray 318 needs to have the characteristic of being substantially transparent to microwaves. A disc made from virgin polytetrafluorethylene works well. The liner heater reduces the process time by preheating the metallic parts of the system, thereby offsetting heat dissipation in the metallic parts of the sterilizer when microwaves are not in use. The means for external control can be any electronic control system, such as a line voltage thermostat.

As stated previously, the flanged ends of the upper and lower outer shells are designed to be held together by a clamp. Preferably, the clamp 116 (FIG. 8) releasably connects the bottom flanged end 122 of the upper outer shell 104 and the top flanged end 240 of the lower outer shell 106 such that the upper 126 and lower 244 coaxial tubes are aimed at each other. The clamp 116 should also allow the clamped microwave waste sterilizer 102 to maintain an internal pressure between 0 Mpa (0 psi) and 1.38 Mpa (200 psi). It has been found that a split ring clamp that forms to a surface of the flanged end at an angle will provide the greatest amount of holding tension with a minimum of pressure to the clamp. Further, the use of an o-ring in the pressure seal area may be employed to act as both a gasket and a relief valve, preventing the sterilizer from over-pressurizing. The flanged ends 240 of the lower outer shell 106 can contain a circumferential groove to accept the o-ring. Compressing the o-ring by the clamping process to a compression of about 20 percent has proven satisfactory.

The microwave waste steam can be made to fit into a superstructure which is only slightly larger than a refrigerator. A hydraulic system, such as those available from Tokyo Sintered Metals Corp., Tokyo, Japan, can be used with good results to open and close the clamp and to raise and lower the upper portion of the sterilizer. The cylinders may be suspended from the top of the superstructure. The lower portion of the sterilizer can be mounted on a drawer to assembly to allow the operator to open the drawer, once the upper portion is raised, and to place or remove the reusable waste container in the lower portion. Any moisture added and condensate formed during the sterilization process can be gathered and recycled as moisture addition for the next cycle. Therefore, an external drain is not necessary.

In another embodiment of the invention, there is provided a method for sterilizing waste materials. The method comprises placing waste materials in a reusable waste container, placing the waste container in a microwave waste sterilizer, clamping the microwave waste sterilizer closed, broadcasting an upper magnetron and a lower magnetron simultaneously so as to generate microwave energy within the microwave waste sterilizer, injecting water into the microwave waste sterilizer, measuring temperature, maintaining a predetermined pressure within the microwave waste sterilizer for a predetermined time period, ceasing the generation of microwave energy, venting the microwave waste sterilizer, opening the waste sterilizer, and removing the waste container. In a preferred embodiment of the process, the lower magnetron unit broadcasts at 180° or at least 120° out of phase from the upper magnetron unit. Also, the water is injected in a predetermined number of batches. The injected water, along with any condensate, can be trapped and recycled for the next cycle, eliminating the need for an outside drain.

The microwave waste sterilizer 102 comprises a generally bell-shaped upper outer shell 104, a generally bowl-shaped lower outer shell 106, an upper means for guiding microwave energy 108 connected to the upper outer shell, a lower means for guiding microwave energy 110 connected to the lower outer shell, an upper means for dispersing microwave energy 112 connected to the upper means for generating microwaves, a lower means for dispersing microwave energy 114 connected to the lower means for generating microwaves, and a clamp 116 releasably holding the upper shell and the lower shell together, all substantially as previously described.

In yet another embodiment of the invention, there is provided a method for dispersing microwave energy into a chamber. The method comprises broadcasting microwave energy across a chamber, reflecting the microwave energy from a surface of the chamber, coupling the microwave energy onto a means for coaxial guidance and changing direction of flow to a new direction of flow substantially parallel to the means for coaxial guidance, propagating the microwave energy in the new direction of flow within a means for guiding microwave energy, splitting the microwave energy in a means for dispersing microwave energy, and broadcasting the dispersed microwave energy into a chamber in a flux field of substantially uniform flux. The microwave energy is split into two paths by the means for dispersing microwave energy and the resultant flux field is substantially cone-shaped.

Referring to the Figures, the chamber used to broadcast microwave energy comprises a substantially rectangular box-shaped waveguide 252 and a coax 272. The waveguide 252 has a first side plate 254 having an outside surface 256, a second side plate 258 substantially parallel to the first side plate and having an outside surface 260, a first movable end block 322 substantially normal to the first and second side plates 254, 258 and a second movable end block 324 substantially parallel to the first movable side plate 322. The first side plate 254 has a first end 262, a second end 264, a first hole 266 between the first end and a center of the first side plate and a second hole 268 near the second end having a diameter smaller than a diameter of the first hole. The second side plate 258 has a hole 270 of a diameter substantially the same as the diameter of the first hole 266 in the first side plate 254. The hole 270 in the second side plate is oriented in axial alignment with the first hole 266 in the first side plate. The first and second movable end blocks 322, 324 each have the characteristic of a tuning short. A magnetron 152' is connected to the first side plate 254 of the waveguide at the second hole 268 so that waves produced by the magnetron are broadcast within the rectangular box-shaped waveguide. The tubular coax 272 has a first end 274, a second end 276, an inside surface defining a diameter substantially the same as the diameter of the first hole 266 in the first side plate of the waveguide, and a longitudinal axis. The first end 274 is connected to the outside surface 256 of the first side plate 254 so that the longitudinal axis is coaxial with the first hole 266 and the coax 272 is in covering relationship to the first hole 266. A tubular conductor plug 278 is closely received by the second end 276 of the coax. The conductor plug 278 has a first end, a second end, an outside diameter substantially the same as the inside diameter of the coax, an inside surface defining a diameter substantially the same as an outside diameter of a coaxial tube 244, and a longitudinal axis. The position of the conductor plug 278 is adjustable within the coax 272 and the conductor plug has the characteristic of a tuning short.

The means for coaxial guidance (FIG. 10) comprises a coaxial tube 244 having an outside surface 246, a first end 248, a second end 250, an outside diameter and a longitudinal axis. The coaxial tube is preferably made from aluminum.

The means for guiding microwave energy comprises a substantially can-shaped z-neck 280 and a generally tubular dielectric disc 292. The z-neck 280 has a first end 282, a flange end 284, a generally tubular sidewall 286 having an outside surface connecting the first end 282 and the flanged end 284 and an inside surface 288 having a diameter greater than the diameter of the hole 270 in the second side plate 258 of the waveguide, and a longitudinal axis. The first end 282 has a hole 290 coaxial with the longitudinal axis and having a diameter substantially the same as a diameter of the hole 270 in the second side plate 258 of the waveguide. This first end 282 is connected to the second side plate 258 of the waveguide so that the hole 290 in the first end 282 is coaxial with the hole 270 in the second side plate and the first end 282 is in covering relationship with the hole 270. The flange end 284 is substantially fin-shaped and has a generally cylindrical inside surface coincident with the inside surface 288 of the z-neck. The z-neck is preferably made from aluminum. The dielectric disc 292 has a first end 502, a second end 504, a longitudinal axis, a first outside surface 506 adjacent to the first end 502 and having a first outside diameter, a second outside surface 508 adjacent to the second end 504 and having a second outside diameter which is greater than the first outside diameter, a first annular shoulder 510 joining the first outside surface 506 and the second outside surface 508 and an inside surface defining a diameter 512 substantially the same as the outside diameter of the coaxial tube 244. The dielectric disc 292 is positioned in the z-neck 280 in covering relationship with the hole 290 in the first end 282 of the z-neck. The dielectric disc has the characteristic of being substantially transparent to microwaves. It has been found that virgin polytetrafluoroethylene works well for the type of microwaves broadcast.

The means for dispersing microwave energy (FIG. 10) comprises a generally tubular adaptor 294, a generally bowl-shaped outer shell 106, an inner liner 296 and a deflector 314. The adaptor 294 has a first end 602, a second end 604, a first inside surface 606 adjacent to the first end 602 and having a first inside diameter, a second inside surface 608 adjacent to the second end 604 and having a second inside diameter smaller than the first inside diameter, a first annular shoulder 610 joining the first inside surface 606 and the second inside surface 608, a first outside surface 612 adjacent to the first end 602 and having a first outside diameter, a second outside surface 614 adjacent to the second end 604 and having a second outside diameter smaller than the first outside diameter, a second annular shoulder 616 joining the first outside surface 612 and the second outside surface 614, and a longitudinal axis. The first inside diameter is substantially the same as the first outside diameter of the dielectric disc 292 so as to closely receive the dielectric disc. The second inside diameter is substantially the same as the diameter of the hole 290 in the first end 282 of the z-neck 280 and the first outside diameter is smaller than the diameter of the inside surface 288 of the z-neck 280 such that the dielectric disc 292 and the adapter 294 nest within the z-neck 280. The adaptor is preferably made from aluminum.

The outer shell 106 (FIG. 14) has an inside surface 236, an outside surface 238, a longitudinal axis and a hole 242 at an apex of the bowl shape. The outside flange surface 125 is connected to the flange end 284 of the z-neck 280 so that the z-neck is in covering relationship to the hole 242 in the apex of the bell shape of the outer shell.

The inner liner 296 (FIG. 24) has a longitudinal axis and two portions, namely, a substantially tubular-shaped portion 298 having an inside surface 300 and an outside surface 302, and a parabolic-shaped bell portion 306 connected to the tubular-shaped portion 298 at a point of transition. The parabolic-shaped portion 306 has a first end 308 which has an inside diameter smaller than an inside diameter of the tubular-shaped portion 298, an inside surface 310 and an outside surface 312. The inner liner 296 is connected to the adaptor 294 at the first end 308 of the parabolic-shaped bell portion such that the outside surface 312 at the first end 308 is closely received by the outside surface 614 of the adaptor 294. The outside surfaces 302, 312 of the tubular-shaped portion 298 and the parabolic-shaped bell portion 306 of the inner liner are adjacent to the inside surface 236 of the outer shell 106. In a preferred embodiment, the liner is constructed from aluminum and is formed by spinning.

The deflector has a first end 702, a second end 704, a first generally frustoconically-shaped outside surface 706 adjacent to the first end 702, a second generally frustoconically-shaped outside surface 708 adjacent to the second end 704, a third generally cylindrical outside surface 710 connecting the first outside surface 706 and the second outside surface 708, and a longitudinal axis. The first frustoconically-shaped outside surface 706 converges away from the first end 702 at an angle of between about 8° and 25°. The second frustoconically-shaped outside surface 708, which mirrors the first frustoconically-shaped surface, converges away from the second end 704 at an angle between about 8° and 25°. The first end 702 is connected to the second end 250 of the coaxial tube 244 such that a common plane passes through the lower deflector and the near 90 degree point of transition between the tubular portion 298 and the parabolic-shaped bell portion 306 of the lower inner liner 296. The deflector is preferably made from aluminum with a magna plate HRC coating.

The longitudinal axes of the outer shell, coaxial tube, coax, conductor plug, z-neck, lower dielectric disc, adaptor, inner liner and deflector are coaxial. Also, the coaxial tube extends through the conductor plug, coax, waveguide, z-neck, lower dielectric disc, adapter, parabolic-shaped bell portion of the inner liner and deflector.

While not wishing to be bound to any theory of operation, it is believed that the microwave energy is split along at least two paths within the means for dispersing microwave energy. The first path is formed by the coaxial tube. The second path is formed by the inside surfaces of the tubular-shaped portion and the parabolic-shaped bell portion of the inner liner. The portion of energy that follows the coaxial tube travels down the coaxial tube to the deflector. The energy traveling along the inside surface of the parabolic-shaped bell portion reaches the point of transition between the parabolic-shaped bell section and the tubular section and changes direction. Much of this energy is directed toward the deflector. A portion of the energy which reaches the deflector is reflected back towards the inner liner, eventually returning to the deflector. Other energy is dispersed from the deflector into a solid cone-shaped flux field. The flux field is substantially uniform, thus eliminating cold spots seen when the microwave energy is narrowly focused. A nipple 316 may be added to the second end 704 of the deflector 314 to further tune the microwave energy which stands off the inner liner at the near 90 degree point of transition between the tubular portion 298 and the parabolic-shaped bell portion 306. The nipple should be cylindrical with a longitudinal axis coaxial with the longitudinal axis of the deflector 314.

Figure 27A:
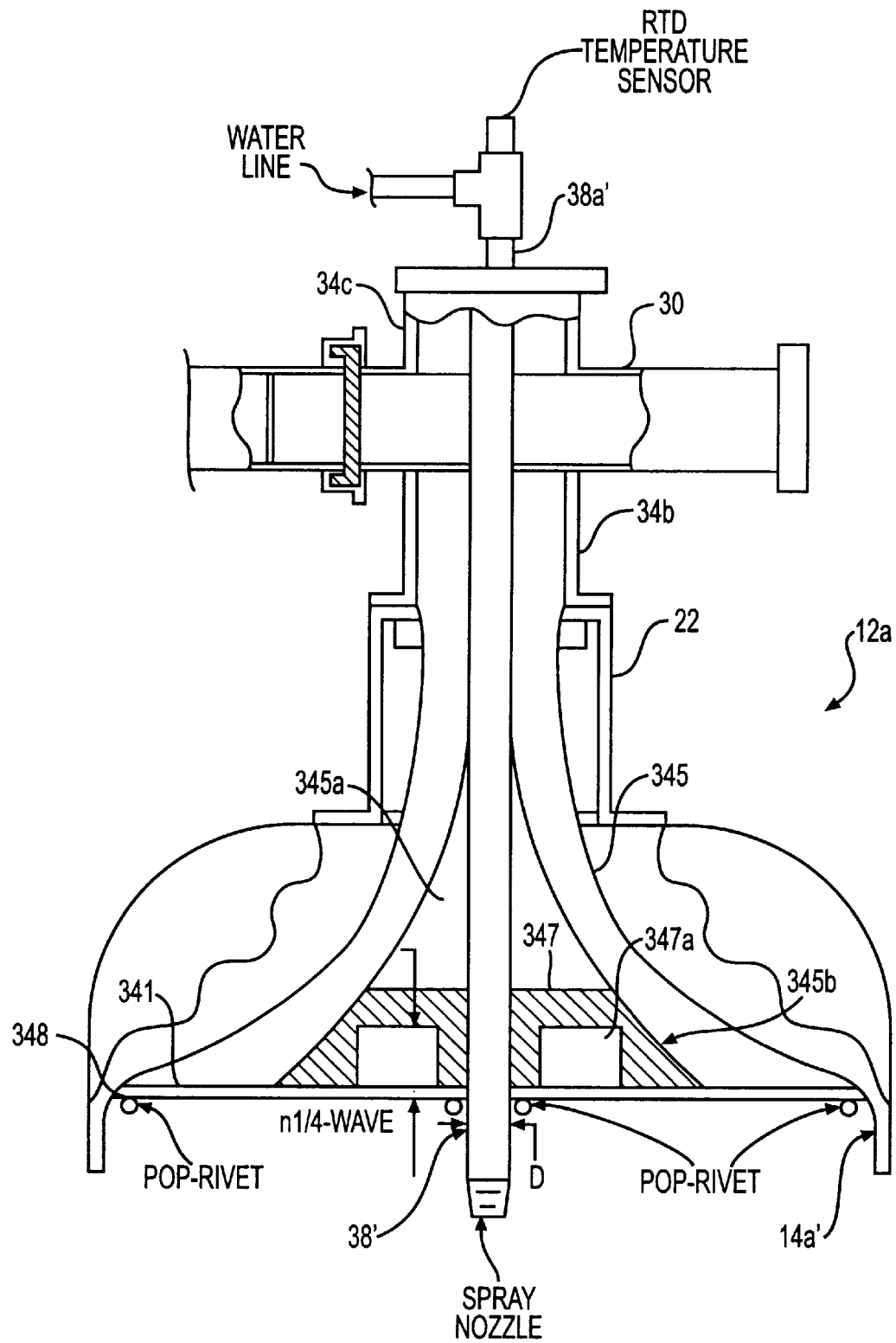
FIGS. 27a–27c illustrate cross-sectional views of the variations of the upper hull in accordance with a second embodiment of the present invention.
Figure 27B:
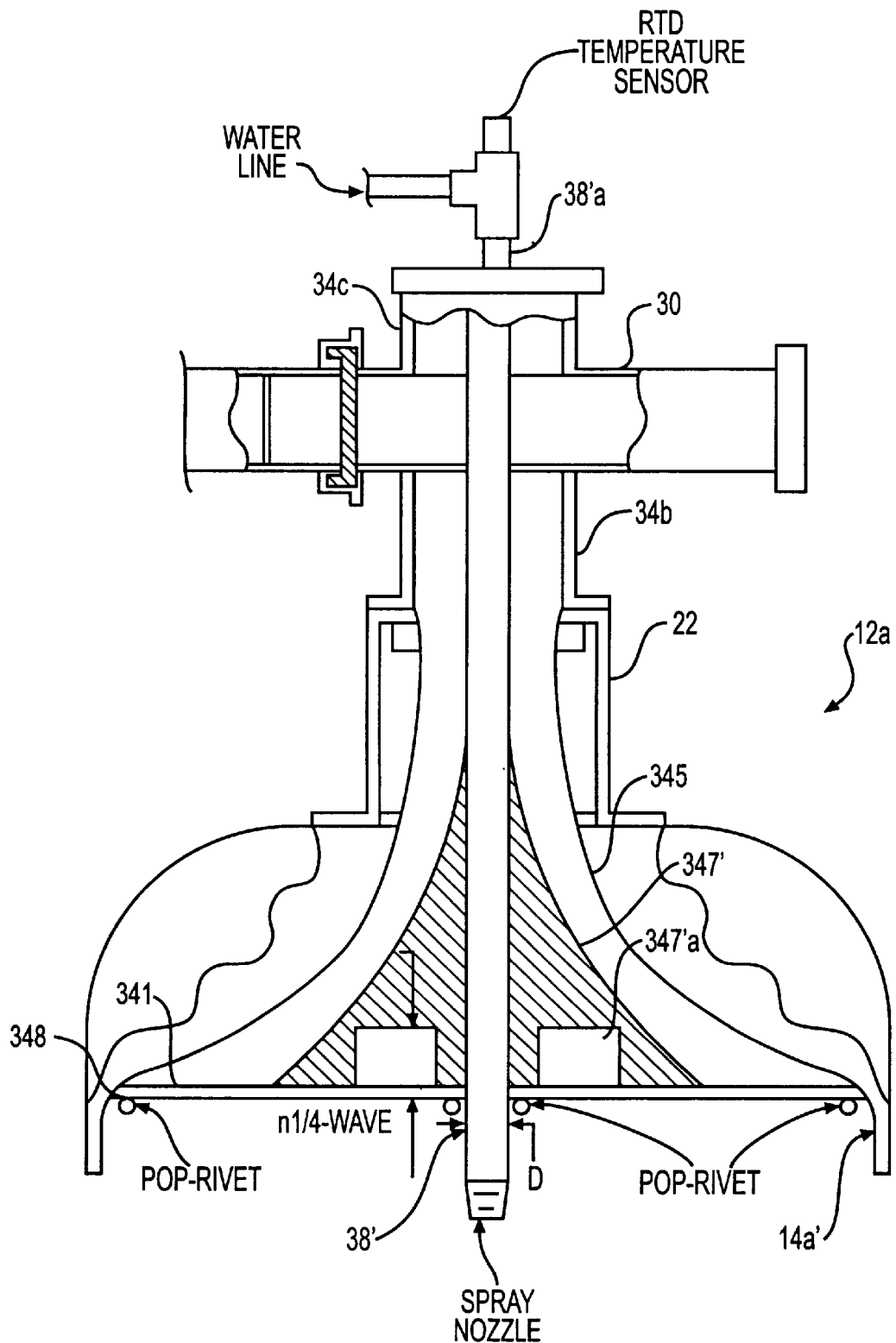
Figure 27C:
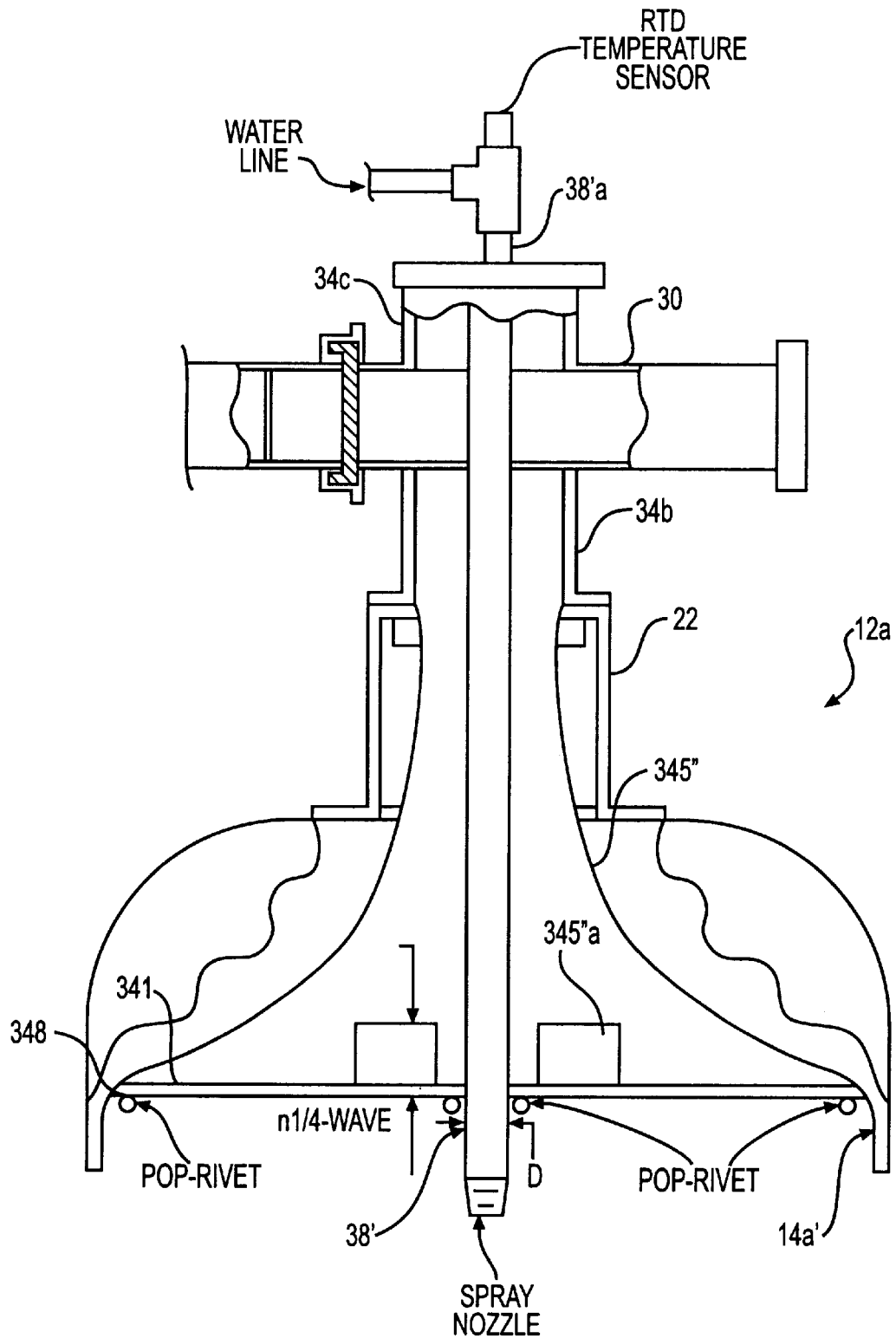

In a second embodiment of the present invention, FIGS. 27a–27c illustrate variations of the upper hull 12a. In the first variation, as shown in FIG. 27a, a hollow, conically-shaped upper outlet conduit 345 is connected at its apex to the first microwave generating assembly 30 positioned atop the vessel 10 (FIG. 1). Specifically, the apex of the upper outlet conduit 345 extends out of the cylindrical neck 22 and into the output waveguide section 34b of the first microwave generating assembly 30. The linear member 38' extends through the first microwave generating assembly 30, as in the first embodiment, but also through and concentric with the upper outlet conduit 345. Unlike the first embodiment, however, the linear member 38' is formed such that its outer end 38'a does not substantially extend beyond the exterior of the microwave generating assembly 30, specifically the first reflective section 34c. The diameter D of the linear member 38' may be enlarged so as to optimize the transmission of microwaves into the treatment chamber 20 (for example, 1.0" I.D.), but only to the extent that its impedance characteristics are not compromised (for example, do not exceed 2.0" O.D.). Diameter D also allows for water feeding I.D. and for RTD temperature sensor.

Within the hollow portion 345a of the upper outlet conduit, a donut-shaped element 347 is fixedly inserted and positioned so as to cover the lower, open base end 345b of the upper outlet conduit. The donut-shaped element 347 made of tungsten or aluminum and is formed with a circular channel 347a on a lower face thereof that is coaxial with the linear member 38' and the upper outlet conduit 345 and opens into the treatment chamber 20. The depth of the channel 347a is defined as n¼-waves in order for the combination of the upper outlet conduit 345 and the element 347 to operate as a n¼-wave shorted line in projecting microwaves into the treatment chamber in a circular pattern with greater bandwidth than the first embodiment. The width of the channel 347a is defined as around 1.5", while the diameter of the channel is set at 2.5". A microwave transparent upper barrier plate 341 is then fixedly positioned on the bottom of the upper-outlet conduit 345, thereby defining the upper ceiling of the treatment chamber 20. To affix the upper barrier plate 341, conventional means such as pop rivets and silicon sealant may be used.

To form the treatment chamber 20, an upper portion 14a' of a liner 14' may be affixed to the upper barrier plate 341 with a sealant material 348 between the outer periphery of the upper barrier plate 341 and the upper portion 14a' to prevent leakage.

In a second variation as shown in FIG. 27b, a conically-shaped element 347' is inserted into the hollow portion 345a of the upper outlet conduit, whereby the interior of the upper outlet conduit 345 is occupied and filled with the element 347'. A circular channel 347'a is also defined on the bottom portion of the element 347' with dimensions and characteristics similar to those of the channel 347a of the first variation. In all other respects the structure and operation of this second variation is the same as those of the first variation.

In a third variation of the upper hull 12a, FIG. 27c shows a solid, conically-shaped upper outlet conduit 345" whose apex extends out of the cylindrical neck 22 and into the output waveguide section 34b of the first microwave generating assembly 30. As with the other variations, the linear member 38' extends through the first microwave generating assembly 30, and through and concentric with the upper outlet conduit 345". A circular channel 345"a is defined on the bottom surface of the conduit 345" concentric with both the linear member 38' and the conduit 345". The dimensions and characteristics of the channel 345"a is also similar to those of the channel 347a of the first variation, while the dimensions and characteristics of the linear member 38" is the same as those of the linear member 38' of the first and second variations.

The upper output conduit, in all of its variation is constructed from aluminum, while the upper barrier plate 341 is formed from micro transparent virgin polytetrafluoroethylene.

Figure 28:
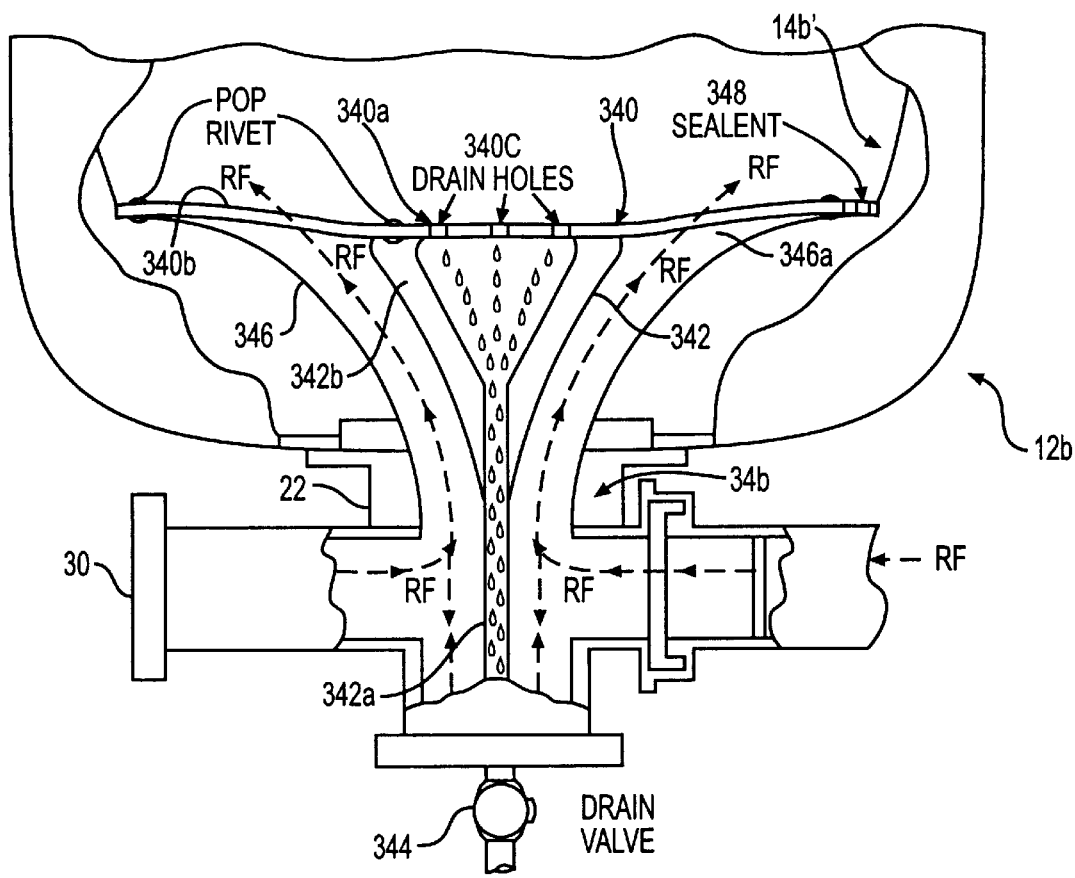
FIG. 28 shows a cross-sectional view of a variation of the lower hull in accordance with the second embodiment of the present invention.

In the corresponding variation of the lower hull 12b (FIG. 28), the second microwave generating assembly 30 positioned underneath the vessel 10 is connected to the apex of an inverted conically-shaped outlet conduit 346 which extends out of the cylindrical neck 22 and integrally formed into the output waveguide section 34b of the second microwave generating assembly 30. An inverted conically-shaped drain member 342 is positioned inside and concentric with the outlet conduit 346. A lower conduit end 342a of the drain member 342 extends through the apex of the outlet conduit 346 and through the microwave generating assembly 30. In this embodiment, the outlet conduit 346 is formed from aluminum and the drain member 342 is also formed from aluminum or stainless steel.

A drain valve 344 is operatively positioned along the lower conduit end 342a outside of and below the second microwave generating assembly 30. One example for the drain valve 344 is an ELS-18 series EL-O-MATIC electric rotary valve actuator. As with the first embodiment, a pressure sensor, similar to the pressure sensor 48, may incorporated along the lower conduit end 342a to monitor the pressure in the treatment chamber, and a filter structure (not shown) may be incorporated between the lower conduit end 342a and the drain valve 344 to prevent particulates from reaching the drain valve.

A vapor barrier plate 340 made of teflon so as to be microwave transparent, is fixedly and sealably mounted atop the upper end 346a of outlet conduit 346 and the upper end 342b of the drain member 342. The vapor barrier plate 340 is formed to be flexed downward toward its center portion 340a into a sink-like shape, whereby condensed water forming on its upper surface 340b will flow by gravity toward the center portion 340a. The center portion 340a is formed with a plurality of drain holes 340c defined therethrough. The upper end 342b of the drain member 342 is fixedly positioned underneath the barrier plate 340 and aligned with the drain holes 340c such that water flowing through the drain holes 340c will flow only into and through the drain member 342. The barrier plate 340 is held in place using, for example, pop rivets, bracket flanges and silicon sealant.

The positioning of the drain member 342 allows it to function mechanically as both a combined drain/sink for condensed water that forms in the pressure vessel 10, and electrically as a center conductor of a coaxial antenna similar to the linear member 38 or the outlet conduit 46. In its function as a combined drain/sink, the drain member 342 automatically scavenges the condensed water, thereby reducing shunt dissipation.

In this variation of the lower hull 12b, the combination of the outlet conduit 346, drain member 342 and barrier plate 340 may be constructed so as to be incorporated into a lower portion 14b' of the liner 14', thereby replacing the outlet conduit 46, the conically shaped member 42, the drain conduits 47, floor member 40 and liner 14 in the first embodiment. The lower portion 14b' of the liner 14' would, for example, be attached to the outer periphery of the barrier plate 340 with a sealant material 348, such as Dow Corning DAP 100% silicone sealant, between them to prevent leakage out of the treatment chamber 20.

Alternatively, this variation of the lower hull 12b may also be constructed so as to replace the lower portion 14b of the liner 14 altogether in addition to the other elements described above. In this case, outer edges of the outlet conduit 346 would simply be extended to surround the barrier plate 340 and inter-engage with the corresponding upper portion 14a of the liner 14 or the outer edges of the upper output conduit 345, whereby the treatment chamber 20 would be fully enclosed when the upper and lower hulls 12a, 12b are locked together.

The operation of this second embodiment of the present invention and all its variants are generally in accordance with the operation of the first embodiment as described in detail hereinabove. For example, the generating of the microwaves and its inputting into the treatment chamber, the feeding of water into the treatment chamber, use of a sensor to monitor the pressure conditions in the pressure vessel, and the use of an electronic controller to automatically control the various stages of the apparatus' operation in the second embodiment are all consistent with the equivalent elements or aspects of the first embodiment. Any modifications to the operation as a result of the differences between the two embodiments would be understood by one of skill in the art given the disclosure of the present invention.

Although the present invention has been fully described in connection with the preferred embodiments thereof with reference to the accompanying drawings, it is to be noted that various changes and modifications will be apparent to those skilled in the art. Such changes and modifications are to be understood as included within the scope of the present invention as defined by the appended claims, unless they depart therefrom.

What is claimed is:

1. A microwave sterilizing apparatus for medical waste, comprising:

a pressure vessel having first and second pressure hulls that are movably engageable with each other so as to form a sealably closed vessel in operation;

a treatment chamber defined within said pressure vessel, and having means for supporting a container of medical waste to be processed and means for receiving and focusing microwaves within said treatment chamber;

means for generating microwaves, said generating means being operatively connected to transmit microwaves into said pressure vessel and said treatment chamber; and means for feeding water into said treatment chamber, whereby steam and pressure are generated within said treatment chamber by operation of said microwave generating means and said feeding means, and a combination of steam, pressure and microwaves in said treatment chamber effects sterilization of said medical waste to be processed, wherein said microwave receiving and focusing means of said treatment chamber includes first and second output elements fixedly mounted in said first and second pressure hulls, respectively, of said pressure vessel, whereby said supporting means is operatively positioned between said first and second output elements, and said microwave generating means includes first and second microwave generating assemblies operatively connected to input microwaves into said pressure vessel and said treatment chamber via said first and second output elements, respectively.

2. A microwave sterilizing apparatus as set forth in claim 1, wherein said pressure vessel further includes means for sealably latching said first and second pressure hulls together such that pressure is containable in the sealably closed vessel formed thereby.

3. A microwave sterilizing apparatus as set forth in claim 1, wherein said treatment chamber includes first and second liner portions, each fixedly positioned within the first and second pressure hulls, respectively, the first and second liner portions being formed to as to surround the medical waste container therein when said pressure vessel forms the sealably closed vessel and to focus the microwaves received in said pressure vessel on the medical waste in the container.

4. A microwave sterilizing apparatus as set forth in claim 3, wherein the first and second liner portions are further shaped to focus and distribute the microwaves in a single mode.

5. A microwave sterilizing apparatus as set forth in claim 1, wherein the supporting means for medical waste container includes a microwave transparent floor member on which the container is positioned, the transparent floor member having defined thereon a plurality of vents through which water condensing in said treatment chamber is drained out.

6. A microwave sterilizing apparatus as set forth in claim 1, wherein the first output element of said means for receiving and focusing microwaves into said pressure vessel includes a linear member having first and second ends, the first end being operatively connected to said first microwave generating assembly and the second end extending into said treatment chamber so as to coaxially transmit the microwaves from said first microwave generating assembly into said treatment chamber.

7. A microwave sterilizing apparatus as set forth in claim 6, wherein said linear member includes a first hollow, conically-shaped capacitor member fixedly connected at an apex thereof to the second end of said linear member, whereby the microwaves transmitted into said treatment chamber are emitted from said linear member as a single mode, microwave field at the medical waste container.

8. A microwave sterilizing apparatus as set forth in claim 6, wherein said water feeding means includes a liquid injection conduit formed in said linear member through which water is fed and sprayed out of the first end of said linear member and into said treatment container.

9. A microwave sterilizing apparatus as set forth in claim 1, wherein the second output element of said means for receiving and focusing microwaves into said pressure vessel includes an outlet conduit having first and second ends, the first end being operatively connected to said second microwave generating assembly and the second end extending into said treatment chamber so as to coaxially transmit the microwaves from said second microwave generating assembly into said treatment chamber.

10. A microwave sterilizing apparatus as set forth in claim 9, wherein said outlet conduit includes a second hollow, conically-shaped capacitor member fixedly connected at an apex thereof to the second end of said outlet conduit, whereby the microwaves transmitted into said treatment chamber are emitted from said outlet conduit as a single mode, microwave field at the medical waste container.

11. A microwave sterilizing apparatus as set forth in claim 8, wherein the supporting means for the medical waste container includes a microwave transparent floor member on which the container is positioned, the transparent floor member having defined thereon a plurality of vents through which water condensing in said treatment chamber is drained out, and said outlet conduit includes at least one drain conduit operatively connected between the plurality of vents and said outlet conduit, whereby water and exhaust gases in said treatment chamber are drained out of said treatment chamber through said outlet conduit.

12. A microwave sterilizing apparatus as set forth in claim 1, wherein the first output element of said means for receiving and focusing microwaves into said pressure vessel includes conically-shaped upper outlet conduit having an apex that is operatively connected to said first microwave generating assembly, and a linear member having first and second ends, the first end being operatively connected to said first microwave generating assembly through the apex of said upper outlet conduit and the second end extending into said treatment chamber, said upper outlet conduit and said linear member being coaxially positioned with one another, whereby said upper outlet conduit and said linear member coaxially transmit the microwaves from said first microwave generating assembly into said treatment chamber.

13. A microwave sterilizing apparatus as set forth in claim 12, wherein said conically-shaped upper outlet conduit is formed as a hollow conduit with a donut-shaped element fixedly covering a lower base end of said upper outlet conduit with said linear member extending therethrough, said donut-shaped element having upper and lower faces, the lower face thereof having a circular channel defined thereon and concentric with said upper outlet conduit and said linear member.

14. A microwave sterilizing apparatus as set forth in claim 13, wherein said conically-shaped upper outlet conduit is formed as a hollow conduit with a conically-shaped element fixedly inserted in said upper outlet conduit with said linear member extending therethrough, said conically-shaped element having a lower face on which a circular channel is defined and concentrically positioned with said upper outlet conduit and said linear member.

15. A microwave sterilizing apparatus as set forth in claim 13, wherein said conically-shaped upper outlet conduit is formed as a solid element with said linear member extending therethrough, said upper outlet conduit having a lower face on which a circular channel is defined and concentrically positioned with said upper outlet conduit and said linear member.

16. A microwave sterilizing apparatus as set forth in claim 13, wherein said water feeding means includes a liquid injection conduit formed in said linear member through which water is fed and sprayed out of the first end of said linear member and into said treatment container.

17. A microwave sterilizing apparatus as set forth in claim 1, wherein the second output element of said means for receiving and focusing microwaves into said pressure vessel includes an inverted, hollow, conically-shaped lower outlet conduit, a lower apex of said lower output conduit being operatively connected to said second microwave generating assembly, and an inverted, conically-shaped, hollow drain member coaxially positioned in said lower output conduit and having a lower conduit end that extends through said lower apex and through the second microwave generating assembly, whereby the lower output conduit and drain member coaxially transmit the microwaves from said second microwave generating assembly into said treatment chamber.

18. A microwave sterilizing apparatus as set forth in claim 17, wherein the supporting means for the medical waste container includes a microwave transparent vapor barrier plate fixedly mounted atop said lower output conduit and on which the container is positioned, the transparent vapor barrier plate having defined thereon a plurality of drain holes located above an open end of said drain member, whereby water and exhaust gases in said treatment chamber are drained out through said drain member.

19. A microwave sterilizing apparatus as set forth in claim 1, further comprising:

means for controlling operation of said microwave sterilizing apparatus.

20. A microwave sterilizing apparatus as set forth in claim 19, wherein said control means is operatively connected to said microwave generating means, and includes sensors for determining pressure and temperature within said treatment chamber, means for evaluating input signals from the sensor, and means for regulating operation of said first and second microwave generating assemblies in response to the input signals from the sensor.

21. A microwave sterilizing apparatus as set forth in claim 20, wherein said control means is operatively connected to said water feeding means so as to control feeding of water into said treatment chamber in response to the input signals from the sensor.

22. A microwave sterilizing apparatus as set forth in claim 19, wherein said control means includes a timer so as to control operation of at least said microwave generating means and said water feeding means in response to operation of said timer.

23. A microwave sterilizing apparatus as set forth in claim 19, further comprising:

an exhaust valve for draining water and exhaust gases from said pressure vessel, said exhaust valve being operatively connected to said control means, whereby opening and closing of said exhaust valve is effected in response to operation of said control means.

24. A microwave sterilizing apparatus as set forth in claim 20, further comprising:

an exhaust valve for removing steam and exhaust gases from said pressure vessel, said exhaust valve being operatively connected to said control means, whereby said control means controls opening and closing of said exhaust valve in response to the input signals from said sensor.

25. A microwave sterilizing apparatus as set forth in claim 19, further comprising:

first motor means for automatedly and alternatingly moving said first and second pressure hulls of said pressure vessel into and out of sealably closed engagement with each other, said first motor means being operatively connected to said control means, whereby said control means automatedly controls the sealably closed engaging and disengaging of said first and second pressure hulls with one another.

26. A microwave sterilizing apparatus as set forth in claim 25, wherein said pressure vessel further includes means for sealably latching said first and second pressure hulls together such that pressure is containable in the sealably closed vessel formed thereby, said apparatus further comprising:

second motor means for automatedly and alternatingly engaging said latching means, said second motor means being operatively connected to said control means, whereby said control means automatedly controls the sealable latching of said first and second pressure hulls with each other.

* * * * *